(12) United States Patent
Wang

(10) Patent No.: US 11,903,956 B2
(45) Date of Patent: Feb. 20, 2024

(54) COMPOSITIONS AND PRODUCTS FOR INFECTIOUS OR INFLAMMATORY DISEASES OR CONDITIONS

(71) Applicant: B&H BIOTECHNOLOGIES, LLC, Willowbrook, IL (US)

(72) Inventor: Huiru Wang, Willowbrook, IL (US)

(73) Assignee: B&H BIOTECHNOLOGIES, LLC, Willowbrook, IL (US)

( * ) Notice: Subject to any disclaimer, the term of this patent is extended or adjusted under 35 U.S.C. 154(b) by 26 days.

(21) Appl. No.: 17/572,021

(22) Filed: Jan. 10, 2022

(65) Prior Publication Data

US 2022/0211733 A1    Jul. 7, 2022

Related U.S. Application Data

(62) Division of application No. 14/775,952, filed as application No. PCT/US2014/025918 on Mar. 13, 2014, now Pat. No. 11,246,878.

(60) Provisional application No. 61/792,984, filed on Mar. 15, 2013.

(51) Int. Cl.

| | | |
|---|---|---|
| *A61K 31/7008* | (2006.01) | |
| *A61K 45/06* | (2006.01) | |
| *A61K 31/198* | (2006.01) | |
| *A61K 9/00* | (2006.01) | |
| *A23K 20/142* | (2016.01) | |
| *A23L 33/17* | (2016.01) | |
| *A23K 20/147* | (2016.01) | |
| *A23L 33/175* | (2016.01) | |
| *A23L 33/10* | (2016.01) | |
| *C07C 321/14* | (2006.01) | |
| *C07H 15/12* | (2006.01) | |
| *A61K 47/02* | (2006.01) | |
| *A61K 9/10* | (2006.01) | |
| *A61K 9/107* | (2006.01) | |
| *A61K 9/08* | (2006.01) | |

(52) U.S. Cl.
CPC ........ *A61K 31/7008* (2013.01); *A23K 20/142* (2016.05); *A23K 20/147* (2016.05); *A23L 33/10* (2016.08); *A23L 33/17* (2016.08); *A23L 33/175* (2016.08); *A61K 9/0019* (2013.01); *A61K 9/0043* (2013.01); *A61K 9/0095* (2013.01); *A61K 31/198* (2013.01); *A61K 45/06* (2013.01); *C07C 321/14* (2013.01); *C07H 15/12* (2013.01); *A23V 2002/00* (2013.01); *A61K 9/08* (2013.01); *A61K 9/10* (2013.01); *A61K 9/107* (2013.01); *A61K 47/02* (2013.01)

(58) Field of Classification Search
CPC .............. A61K 31/7008; A61K 31/198; A61K 9/0043; A61K 9/0019; A61K 9/0095; A23K 20/142; A23K 20/147; A23L 33/17; A23L 33/175; A61P 37/00; A61P 31/20; A61P 31/16; A61P 31/14; A61P 31/12; A61P 29/00; A61P 11/06; A61P 11/00; A61P 1/12; A61P 1/06
See application file for complete search history.

(56) References Cited

U.S. PATENT DOCUMENTS

| | | | |
|---|---|---|---|
| 4,698,332 | A | 10/1987 | Ogasawara |
| 5,763,483 | A | 6/1998 | Bischofberger |
| 10,202,439 | B2 | 2/2019 | Wang |
| 11,246,878 | B2 | 2/2022 | Wang |
| 2011/0085981 | A1 | 4/2011 | Wang |
| 2012/0142619 | A1 | 6/2012 | Jin |
| 2019/0270792 | A1 | 9/2019 | Wang |

FOREIGN PATENT DOCUMENTS

| | | |
|---|---|---|
| CN | 102178666 | 9/2011 |
| CN | 102002077 B | 8/2014 |
| CN | 102178686 B | 1/2016 |

OTHER PUBLICATIONS

Calder et al., British Journal of Nutrition, 2009, 101(S1), p. 1-45. (Year: 2009).*
Definition of prevent, Oxford English Dictionary Online, http://dictionary.oed.com/, accessed online Mar. 27, 2010, especially definition 9a. at p. 2. (Year: 2010).*
Krausslich et al., Antiviral Strategies, Handbook of Experimental Pharmacology, 2009, Springer-Verlag Berlin Heidelberg, p. 1-24. (Year: 2009).*
De Clercq, E., "Antiviral drugs in current clinical use," J. Clin. Viral., 30, p. 115-133 (2004).
Ilyushina et al., "Combination chemotherapy, a potential strategy for reducing the emergence of drug-resistant influenza A variants," Antiviral Research, 70, p. 121-131 (2006).
Levin, et al., "Principles of Combination Therapy," Bull. N. Y. Acad. Med., 51(9), p. 1020-1038 (1975).
Ross, Z. M. "Antimicrobial Properties of Garlic Oil against Human Enteric Bacteria: Evaluation of Methodologies and Comparisons with Garlic Oil Sulfides and Garlic Powder" Applied and Environmental Microbiology, 67, Jan. 2001, p. 475-480.
European search Report, dated Jan. 1, 2017, issued for application No. EP14770180, filed on Mar. 13, 2014. 8 Pages.

(Continued)

*Primary Examiner* — Jonathan S Lau
(74) *Attorney, Agent, or Firm* — Morrison & Foerster LLP

(57) ABSTRACT

Composition and methods for treating infectious and inflammatory diseases using saccharide based products and therapies. Products can be implemented as a nutritional supplement, a food, a feed, a food additive, a feed additive, a therapeutic product, a rehydration salt, or a rehydration solution. The present disclosure relates generally to the fields of compositions and products containing the compositions, and the use of the compositions or the products for preventing and/or treating infectious or inflammatory diseases or conditions in particular gastrointestinal and respiratory diseases (diarrhea and influenza infections) or inflammatory.

6 Claims, No Drawings

(56) References Cited

OTHER PUBLICATIONS

European search Report, dated Jan. 22, 2020, issued for application No. EP19181779, filed on Mar. 13, 2014. 8 Pages.
International Preliminary Report on Patentability, dated Sep. 15, 2015, issued for PCT/US2014/025918, filed on Mar. 13, 2014. 6 Pages.
Unpublished U.S. Appl. No. 18/448,089, filed Aug. 10, 2023, titled "Biological Therapeutics for Infection-Relating Disorders or Conditions ," (Copy not submitted herewith pursuant to the waiver of 37 C.F.R. § 1.98(a)(2)(iii)).
Yang et al. (2008). "Effective prevention and treatment of Helicobacter pylori infection using a combination of catechins and sialic acid in AGS cells and BALB/c mice," J Nutr. 138(11):2084-90.

* cited by examiner

COMPOSITIONS AND PRODUCTS FOR INFECTIOUS OR INFLAMMATORY DISEASES OR CONDITIONS

CLAIM OF PRIORITY

This application is a divisional of U.S. patent application Ser. No. 14/775,952, filed Sep. 14, 2015, which is a national stage application under 35 U.S.C. § 371 of International Application No. PCT/US2014/025918, filed Mar. 13, 2014, which claims priority to U.S. Provisional Patent Application Ser. No. 61/792,984, filed Mar. 15, 2013, entitled "Compositions and Products for Infectious or Inflammatory Diseases or Conditions." The entirety of the disclosure of each of these applications is hereby incorporated by reference.

FIELD OF INVENTION

The present disclosure relates generally to the fields of compositions and products containing the compositions, and the use of the compositions or the products for preventing and/or treating infectious or inflammatory diseases or conditions in particular gastrointestinal and respiratory diseases (diarrhea and influenza infections) or inflammatory. More specifically, the present disclosure relates to the compositions of oral rehydration salt or oral rehydration solution (ORS) and the use of the ORS for the prevention and treatment of dehydration due to diarrhea or fever. More specifically, the present disclosure relates to the methods of preparing and using the compositions or the products containing the compositions.

BACKGROUND

An infectious disease is a clinically evident disease of humans or animals. Information collected by the World Health Organization (WHO) on global deaths shows that worldwide mortality due to infectious diseases is as high as 25.9% of all deaths, or 14.7 million deaths in 2002 (WHO World Health Report 2002). The current numbers are even higher.

Influenza infections especially an influenza pandemic threats people's health and economy globally. There is a big concern on a possible influenza pandemic causing by highly pathogenic H5N1 (avian or bird) influenza virus which will cause much more deaths than the 2009 swine influenza pandemic (WHO). Currently, there are no effective medicines for the treatment of a serious condition of an influenza infection especially a serious condition after 48 hours of an influenza infection.

The estimated annual incidence of diarrheal diseases by the World Health Organization (WHO) was as high as ~4.51 billion. In 2009 diarrhea was estimated to have caused 1.1 million deaths in people aged five and over and 1.5 million deaths in children under the age of five. Rotaviruses are a leading cause of severe diarrheal disease and dehydration in infants and young children throughout the world especially the third world. Diarrheal diseases are serious problems in animal field too and negatively impact the agriculture-food economy, food safety, public health and the environment.

There is no specific medical treatment for rotavirus infection and other viral diarrhea thus far. Oral rehydration therapy (ORT) with oral rehydration solution (ORS) is now routinely used to correct the fluid and electrolyte losses caused by diarrhea or fever. ORS is used to correct the symptom of dehydration due to diarrhea but does not have anti-diarrheal action (reduced volume and duration).

Farmers routinely give antibiotics to food-producing animals to treat illnesses (e.g. diarrhea), prevent infection and encourage growth. However, mounting evidence indicated that overuse of antibiotics could induce a global crisis of antibiotic-resistant bacteria that do not respond to medical treatment and endanger human lives. The European Union banned the feeding of antibiotics and related drugs to livestock for growth promotion in 2006. The US Food and Drug Administration (FDA) urged farmers to stop giving antibiotics to cattle, poultry, hogs and other animals to spur their growth. Non-antibiotic products capable of replacing antibiotics for the uses mentioned above are needed.

SUMMARY OF THE INVENTION

Aspects of the present disclosure are related to non-antibiotic compositions and the products containing the compositions as: 1) dietary supplements to help supporting or enhancing the protective structure or function of gastrointestinal and respiratory tracts; 2) food or feed additives for the prevention or treatment of infectious or inflammatory diseases or conditions in particular gastrointestinal respiratory diseases or conditions (e.g. diarrhea and influenza infections); 3) therapeutic products for the prevention and treatment of infectious or inflammatory diseases or conditions in particular gastrointestinal respiratory diseases or conditions (e.g. diarrhea and influenza infections); and 4) oral rehydration salt or oral rehydration solution (ORS) for the prevention and treatment of dehydration due to diarrhea or fever. Another aspect of the present disclosure is related to the methods of preparation and the uses of the compositions and the products containing the compositions for the preventing or treating infectious or inflammatory diseases or conditions in particular gastrointestinal respiratory diseases or conditions (e.g. diarrhea and influenza infections) of humans and animals.

In one embodiment the present invention discloses the compositions or products comprise a sialic acid alone or a sialic acid plus at least one of the other major components of the present disclosure. The major components of the present disclosure include but not limited to: 1) a sialic acids including but not limited to N-acetylneuraminic acid, 2-Keto-3-deoxynononic acid, N-Acetylglucosamine, N-Acetylgalactosamine, N-Acetylmannosamine, and N-Glycolylneur-aminic acid; 2) the derivatives or analogs of a sialic acid (e.g. N-Acetylneuraminic acid methyl ester); 3) an other glycan including but not limited to fructose, glucose, mannose, fucose, xylose, galactose, lactose; 4) a glycan modifying molecules including but not limited to sulfur-containing amino acids (e.g. methionine and methionine-zinc complex); and 5) nutritional or pharmaceutically acceptable salts include but not limited to sodium chloride, potassium chloride, sodium citrate, or the oral rehydration salts recommended by WHO.

Examples of compositions or products of the present disclosure include but not limited to the composition or products comprising suitable amount of 1) a sialic acid (e.g. N-acetylneuraminic acid) alone; 2) or the sialic acid (e.g. N-acetylneuraminic acid) plus a glycan modifying molecule (e.g. methionine); 3) or the sialic acid (e.g. N-acetylneuraminic acid) plus an analog of the sialic acid (e.g. N-Acetylneuraminic acid methyl ester); 4) or the sialic acid (e.g. N-acetylneuraminic acid) plus the glycan modifying molecule (e.g. methionine) plus the analog of the sialic acid (e.g. N-Acetylneuraminic acid methyl ester); 5) or a ORS containing suitable amount of a sialic acid (e.g. N-acetylneuraminic acid) alone; 2) or the sialic acid (e.g. N-acetylneuraminic acid) plus a glycan modifying molecule (e.g. methionine); 3) or the sialic acid (e.g. N-acetylneuraminic acid) plus an analog of the sialic acid (e.g. N-Acetylneuraminic acid methyl ester).

Examples of gastrointestinal diseases or conditions of the present disclosure include but not limited to diarrhea, gastroenteritis, ileitis, colitis, coeliac disease, inflammatory bowel disease, Crohn's disease and ulcerative colitis, irritable bowel syndrome (IBS), chronic functional abdominal pain, pseudomembranous colitis, esophagitis, gastritis, esophageal cancer, gastric cancer, intestinal cancer, colon cancer, and colorectal cancer.

Examples of respiratory diseases or conditions of the present disclosure include but not limited to influenza infections, common cold, sinusitis, tonsillitis, otitis media, pharyngitis, laryngitis, viral or bacterial pneumonia, asthma, acute respiratory distress syndrome, emphysema, obstructive pulmonary disorder and lung cancer.

Examples of inflammatory conditions of the present disclosure include but not limited to Alzheimer's, ankylosing spondylitis, arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus erythematous (SLE), nephritis, Parkinson's disease and ulcerative colitis.

Examples of humans of the present disclosure include but not limited to males and females, newborns, 1-12 months old infants, 1-18 years old children, adults, old people, pregnant and feeding females.

Examples of animals of the present disclosure include but not limited to livestock, poultry, companion animals or pets, aquaculture organisms and aquatic animals.

DETAILED DESCRIPTION OF THE PREFERRED EMBODIMENT(S)

While the present disclosure is susceptible of embodiment in many different forms, there will be described herein in detail, preferred and alternate embodiments of the present disclosure. It should be understood however, that the present disclosure is to be considered an exemplification of the principles of the invention and is not intended to limit the spirit and scope of the invention and/or claims of the embodiments illustrated.

Definitions: As used herein

Infectious diseases: refers to the invasion of a host organism's bodily tissues by disease-causing organisms, their multiplication, and the reaction of host tissues to these organisms and the toxins they produce. A short-term infection is an acute infection. A long-term infection is a chronic infection. Pathogens specific to infectious diseases suitable for use in this process include, but are not limited to viruses, bacteria, parasites, fungi, viroids, prions, protozoa, and insects, and etc., without limitation. Examples of infections include but not limited to the disorders caused by influenza viruses, reoviruses, rotaviruses, cytomegaloviruses (CMV), Epstein-Barr viruses (EBV), adenoviruses, hepatitis viruses including HAV, HBV, HCV, human immunodeficiency virus (HIV), human T-cell leukemia viruses (HTLV), human papilloma viruses (HPV), polio viruses, parainfluenza viruses, measles viruses, mumps viruses, respiratory syncytial viruses (RSV), human herpes viruses (HHV), herpes simplex virus (HSV), Varicella-Zoster Virus, cholera viruses, pox virus, rabies virus, distemper virus, foot and mouth disease viruses, rhinoviruses, Newcastle disease viruses, pseudorabies virus, cholera, syphilis, anthrax, leprosy and bubonic plague, rickettsias, *neisseria gonorrhoeae, bordetella pertussis, escherichia coli, salmonella enterica, vibrio cholerae, pseudomonas aeruginosa, yersinia pestis, francisella tularensis, haemophilus influenzae, purple sulfur bacteria, helicobacter pylori, campylobacter jejuni, bacillus anthracis/cereus/thuringiensis, clostridium tetani, clostridium botulinum, staphylococci, streptococci,* pneumococci, *streptococcus pneumoniae, mycoplasmas, bacteroides fragilis, mycobacterium tuberculosis, mycobacterium leprae, corynebacterium diphtheriae, treponema pallidum, borrelia burgdorferi, chlamydia trachomatis, chlamydia psittaci*, phycocyanin, phycoerythrin, mitochondria, chloroplasts, etc without limitation.

Inflammation: refers to the complex biological response of vascular tissues to harmful stimuli, such as pathogens, damaged cells, or irritants. The classical signs of acute inflammation are pain, heat, redness, swelling, and loss of function. Although infection is caused by a microorganism, inflammation is one of the responses of the organism to the pathogen. However, inflammation is a stereotyped response, and therefore it is considered as a mechanism of innate immunity. Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process. Progressive destruction of the tissue would compromise the survival of the organism. However, chronic inflammation can also lead to a host of diseases, such as hay fever, periodontitis, atherosclerosis, rheumatoid arthritis, and even cancer (e.g., gallbladder carcinoma). Examples of inflammation include but not limited to Alzheimer's, ankylosing spondylitis, arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus erythematous (SLE), nephritis, Parkinson's disease, ulcerative colitis, etc without limitation.

Infection-relating diseases or conditions: refers to the disorders or conditions occurred during or after an infection or a vaccination. According to the present invention, infection-relating diseases or conditions include but not limited to autoimmune diseases, allergies, inflammation and tumors occurred during or after an infection or a vaccination. The disorders or conditions usually arise after a period time (e.g. within 4-8 weeks) of an infection or a vaccination. Examples of infection-relating diseases, allergies inflammation and tumors include but not limited to Guillain-Barre syndrome, autism, Kawasaki's disease, biliary atresia, primary biliary cirrhosis, systemic lupus erythematous, leukemia, acute leukemia, rheumatoid arthritis, adult onset diabetes mellitus (Type II diabetes), Sjogren's syndrome, juvenile onset diabetes mellitus, Hodgkin's and non-Hodgkin's lymphoma, malignant melanoma, cryoglobulinemia, hepatitis B virus infection, hepatitis C virus infection, Wegener's granulomatosis, inflammatory bowel disease, polymyositis, dermatomyositis, multiple endocrine failure, Schmidt's syndrome, autoimmune uveitis, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, autoimmune hemolytic anemia, dermatitis herpetiformis, alopecia areata, autoimmune cystitis, pemphigoid, scieroderma, progressive systemic sclerosis, CREST syndrome (calcinosis, Raynaud's esophageal dysmotility, sclerodactyly, and telangiectasia), male or female autoimmune infertility, ankylosing spondylitis, ulcerative colitis, Crohn's disease, mixed connective tissue disease, polyarteritis nodosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multifonne, pemphigus vulgaris, pemphigus, bullous pemphigoid, postcardotomy syndrome, Cushing's syndrome, autoimmune chronic active hepatitis, bird-fancier's lung, asthma, allergic disease, allergic encephalomyelitis, toxic necrodermal lysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, chronic fatigue syndrome, fibromyalgia, Takayasu's arteritis, polymyalgia rheumatica, temporal arteritis, schistosomiasis, giant cell arteritis, ascariasis, aspergillosis, Sampter's syndrome (triaditis also called, nasal polyps, eosinophilia, and asthma), Behcet's disease, Caplan's syndrome, dengue, encephalomyositis, endocarditis, myocarditis, endomyocardial fibrosis, endophthalmitis, erythema elevatum et diutinum, psoriasis, erythroblastosis fetalis, fascitis with eosinophilia, Shulman's syndrome, Felty's syndrome, filariasis, cyclitis, chronic cyclitis, heterochromic cyclitis, Fuch's cyclitis, IgA nephropathy, Henoch-Schonlein purpura, glomerulonephritis, graft versus host disease, transplantation rejection, cardiomyopathy, Alzheimer's disease, parvovirus infection, rubella virus infection, post vaccination syndromes, congenital rubella infection, renal cell carcinoma, multiple myeloma, Eaton-Lambert syndrome, relapsing polychondritis, Waldenstrom's macroglobulinemia, mumps virus infection, thrombotic throbocytopenic purpura, and any other disorder or conditions in which the specific recognition of the host by pathogen-inducible or vaccine-inducible antibodies is suspected or shown to be important in any aspect of the pathogenesis of the clinical illness.

Serious adverse reactions of vaccines or therapeutic antibodies: refers to the severe disorders or conditions caused by harmful antibodies induced during a vaccination or an antibody therapy. The disorders or conditions usually arise after a period time (e.g. within 4-8 weeks) of a vaccination or an antibody therapy. Examples of serious adverse reactions of vaccines of the present disclosure include but not limited to deaths, acute infant death syndrome, Guillain-Barre syndrome, Kawasaki's disease, acute leukemia, allergies, serious allergic reactions, asthma, epilepsy, immune system disorders, behavior disorders, nervous system injury, permanent brain damage, learning difficulties, seizure, severe seizures, lowered consciousness, autism, long-term coma, headaches, upper or low respiratory tract infection, joint pain, abdominal pain, cough, nausea, diarrhea, high fever, blood in the urine or stool, pneumonia, inflammation of the stomach or intestines, non-stop crying, fainting, deafness, temporary low platelet count, hives, pain in the joints, intussusception, vomiting, severe nervous system reaction, life-threatening severe illness with organ failure, still birth, neonatal deaths, and any other disorder or conditions in which an infection of the host is suspected or shown to be important in any aspect of the pathogenesis of the clinical illness.

The respiratory tract: refers to the structures of the anatomy involved with the process of respiration. The respiratory tract is divided into 3 segments: upper respiratory tract including nose and nasal passages, paranasal sinuses, and throat or pharynx; respiratory airways including voice box or larynx, trachea, bronchi, and bronchioles; and lungs including respiratory bronchioles, alveolar ducts, alveolar sacs, and alveoli. Most of the respiratory tract exists merely as a piping system for air to travel in the lungs, and alveoli are the only part of the lung that exchanges oxygen and carbon dioxide with the blood. The respiratory tract is a common site for infections. Upper respiratory tract infections are probably the most common infections in the world.

Respiratory diseases or conditions: refers to an abnormal status or conditions of the upper respiratory tract, trachea, bronchi, bronchioles, alveoli, pleura and pleural cavity, and the nerves and muscles of breathing. Respiratory diseases range from mild and self-limiting. Respiratory diseases can be classified as many types. Inflammatory lung disease include but not limited to asthma, cystic fibrosis, emphysema, chronic obstructive pulmonary disorder or acute respiratory distress syndrome. Obstructive lung diseases include but not limited to chronic obstructive pulmonary disease (COPD), which includes emphysema and asthma. Asthma is a difficulty in breathing causing wheezing due to inflammation of bronchi and bronchioles, this causes a restriction in the airflow into the alveoli. Respiratory tract infections can affect any part of the respiratory system. The upper respiratory tract infection include but not limited to common cold, sinusitis, tonsillitis, otitis media, pharyngitis and laryngitis. The lower respiratory tract infection include but not limited to pneumonia, a lung infection. Pneumonia is usually caused by bacteria, particularly *Streptococcus pneumoniae* in Western countries. Worldwide, tuberculosis is an important cause of pneumonia. Other pathogens such as viruses and fungi can cause pneumonia for example severe acute respiratory syndrome and pneumocystis pneumonia. A pneumonia may develop complications such as a lung abscess, a round cavity in the lung caused by the infection, or may spread to the pleural cavity. Other examples of respiratory diseases or conditions include but not limited to influenza infections, common cold, entities like viral or bacterial pneumonia, pulmonary embolism, and lung cancer.

Gastrointestinal diseases or conditions: refers to an abnormal status or function of the esophagus, stomach and intestine. Examples of gastrointestinal diseases or conditions include but not limited to diarrhea, gastroenteritis, ileitis, colitis, coeliac disease, inflammatory bowel disease, Crohn's disease and ulcerative colitis, irritable bowel syndrome (IBS), chronic functional abdominal pain, pseudomembranous colitis, esophagitis, gastritis, esophageal cancer, gastric cancer, intestinal cancer, colon cancer, and colorectal cancer, Diarrhea: diarrhea is defined by the WHO as having three or more loose or liquid stools per day, or as having more stools than is normal for that person. The same definition is also suitable for animals.

Diarrhea may be caused by an infection or a chronic gastrointestinal disease. The common causes of diarrhea include but not limited to: 1) bacterial infections such as infections caused by *Clostridium, Campylobacter, Salmonella, Shigella, Giardia* and *Escherichia coli;* 2) Viral infections such as infections caused by rotavirus, coronavirus, Norwalk virus, cytomegalovirus, herpes simplex virus and viral hepatitis; 3) nutritional problems or food intolerances. Some people are unable to digest certain component of food such as lactose; and nutritional diarrhea is most common in orphaned animals as a result of dietary changes, poor quality milk replacers, mixing errors, and overfeeding. 4) parasites such as *Giardia lamblia, Entamoeba histolytica*, and *Cryptosporidium;* 5) reactions to medicines such as antibiotics, blood pressure medications and antacids containing magnesium; 6) inflammatory gastrointestinal diseases such as inflammatory bowel disease (IBD) or celiac disease, tuberculosis, colon cancer, and enteritis; 7) functional bowel disorders such as irritable bowel syndrome.

Dehydration: dehydration is defined as the excessive loss of body fluid.

Rehydration: rehydration is defined as the correction of a dehydrated state by the replenishment of electrolytes through oral rehydration therapy or fluid replacement by intravenous therapy.

ORT: refers to Oral rehydration therapy.

ORS: refers to oral rehydration solution or salt.

Intravenous rehydration: refers to the replenishment of electrolytes by intravenous therapy.

Food: refers to any substance consumed to provide nutritional support for the body of an organism including a human or an animal. It is usually of plant or animal origin, and contains essential nutrients, such as carbohydrates, fats, proteins, vitamins, or minerals. The substance is ingested by an organism and assimilated by the organism's cells in an effort to produce energy, maintain life, or stimulate growth.

Feed: refers to any foodstuff that is used specifically to feed domesticated livestock or poultry, companion animals, or farmed aquaculture organisms kept in water.

Food additive: refers to any substances (both natural and artificial origin) added to foods.

Feed additive: refers to any substances (both natural and artificial origin) added to feeds.

Medicated feed or food additive (MFD): refers to any substances added to feed or food intending to cure, treat, prevent or mitigate a disease or a condition or a product that is intended to alter the structure or function of the body (unless it is a food that does that itself).

Dietary supplement: also known as food supplement or nutritional supplement, is a substance or a preparation intended to supplement the diet or provide nutrients that may be missing or may not be consumed in sufficient quantities in a diet of a human or animal individual.

Livestock: refers to one or more domesticated animals raised in an agricultural setting to produce commodities such as food, fiber and labor. The term "livestock" as used in this disclosure does not include poultry or farmed fish; however the inclusion of these, especially poultry, within the meaning of "livestock" is common. Examples of livestock include but not limited to cows, pigs, horses, sheep or goats, llamas, cattle, donkeys.

Poultry: refers to one or more domesticated birds kept by humans for the purpose of collecting their eggs, or killing for their meat and/or feathers. Examples of poultry include but not limited to chickens, ducks, gooses, turkeys and pigeons.

Companion animals or pet: refers to a household animal kept for companionship and a person's enjoyment. Pet includes but not limited to dogs, cats, rabbit, birds, rodent pets such as gerbils, hamsters, chinchillas, fancy rats, and guinea pigs; avian pets such as canaries, parakeets, and parrots; reptile pets, such as turtles, lizards and snakes; and aquatic pets, such as tropical fish and frogs.

Aquaculture organisms: refers to the organisms of the aquatic farming such as fish, shrimp, oyster, crustaceans, molluscs and aquatic plants.

An aquatic animal is an animal, either vertebrate or invertebrate, which lives in water for most or all of its life.

The Major Components of Compositions or Products

The major component of the compositions or products of the present disclosure include but not limited to sialic acids, the derivatives or analogs of the sialic acid, other saccharides, saccharide modifying molecules; and nutritional or pharmaceutically acceptable salts.

Sialic Acid

The major component of the compositions or products of the present disclosure comprises sialic acids. A sialic acid (Sia) is a generic term for the N- or O-substituted derivatives of neuraminic acid, a nine-carbon monosaccharide. It is also the name for the most common member of this group, N-acetylneuraminic acid (Neu5Ac or NANA) and 2-Keto-3-deoxynononic acid (Kdn). Other members of sialic acids include but not limited to N-Acetylglucosamine (GlcNAc), N-Acetylgalactosamine (GalNAc), N-Acetylmannosamine (ManNAc), and N-Glycolylneur-aminic acid (Neu5Gc). The amino group bears either an acetyl or a glycolyl group as described below.

A sialic acid can be included alone or in combination with other components of the present disclosure. N-acetylneuraminic acid can be used as an acidic reagent to achieve a desired pH value of a composition or a product solution.

The amounts or concentrations of a sialic acid in a composition or a product of the present disclosure is from about 0.01 mg/ml to about 900 mg/ml or 0.01 mg/g to about 900 mg/g.

Sialic acids are found widely distributed in human or animal tissues, especially in glycoproteins and gangliosides. N-acetylneuraminic acid can be either isolated from natural materials or artificially synthesized with following characteristics.

Molecular formula: $C_{11}H_{19}NO_9$.

Molecular weight: 309.3.

Structure: See right

Derivatives or Analogs of Sialic Acids

Another major component of the

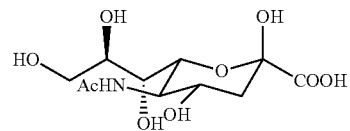 [SMILES: CC(=O)NC1C(O)CC(O)(C(=O)O)OC1[C@H](O)[C@H](O)CO]

compositions or products of the present disclosure comprises any molecules having the general chemical structure of

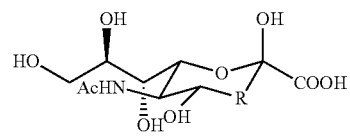

wherein R is a hydrogen, alkyl, cycloalkyl, sodium (Na), substituted alkyl, substituted cycloalkyl, aryl, or substituted aryl, ether, thioester, S—CH$_2$—CH$_3$, disulfide ester, S—CH$_3$, disulfide methyl, methionine, methionine-zinc or phenol or phenol derivatives.

Another major component of the compositions or products of the present disclosure comprises any other derivatives of sialic acids, and/or any other relevant or similar molecules of sialic acids, or any other forms of sialic acids identified as the active ingredient.

The derivatives of sialic acids can be included alone or in combination with other components of the present disclosure.

The amounts or concentrations of a derivative of sialic acids in a composition or a product of the present disclosure is from about 0.01 mg/ml to about 900 mg/ml or 0.01 mg/g to about 900 mg/g.

The hydroxyl substituents of sialic acids may vary considerably: acetyl, lactyl, methyl, sulfate and phosphate groups have been found. The other hydroxyl substituents of sialic acids include but not limited to crotonyl-, succinyl-, propionyl-, butyryl- and sulfur-groups.

One example of a derivative or analog of N-Acetylneuraminic acid is N-Acetylneuraminic acid methyl ester as shown below.

Molecular weight: 323.3
Formula: C$_{12}$H$_{21}$NO$_9$
Structure: See right

The amounts or concentrations of the N-Acetylneuraminic acid methyl ester in a

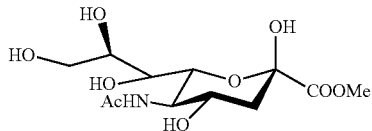

composition or a product of the present disclosure is from about 0.005 mg/ml to about 900 mg/ml or 0.005 mg/g to about 900 mg/g.

Other Saccharides

Another major component of the compositions or products of the present disclosure comprises other saccharides beside sialic acids. The term of the other saccharides of the present disclosure refers to a monosaccharide, an oligosaccharide or a polysaccharide. Monosaccharides include but not limited to fructose, glucose, mannose, fucose, xylose, galactose, lactose. An oligosaccharide is a saccharide polymer containing a small number (typically three to ten) of component sugars, also known as simple sugars.

The other saccharides (e.g. a galactose or a lactose) of the present disclosure include but not limited to O-GlcNAc, GAG Chain, glycosaminosaccharides, and glycosphinglipid. Saccharides usually consist of O-or N-glycosidic linkages of monosaccharides to compatible amino acid side chains in proteins or to lipid moieties. O-and N-linked saccharides are very common in eukaryotes but may also be found, although less commonly, in prokaryotes. Saccharides can be found attached to proteins as in glycoproteins and proteosaccharidess. They are generally found on the exterior surface of cells.

The other saccharides (e.g. a galactose or a lactose) of the present disclosure can be included alone or in combination with a sialic acid or other components of the present disclosure.

The amounts or concentrations of other saccharides (e.g. a galactose or a lactose) in a composition or a product of the present disclosure is from about 0.01 mg/ml to about 900 mg/ml or 0.01 mg/g to about 900 mg/g.

One Example of Other Saccharide is
Saccharide Modification Molecules

Another major component of the compositions or products of the present disclosure comprises saccharide modification molecules. As used herein, saccharide modification molecules refers to molecules containing acetyl-, lactyl-, methyl-, phosphate-, crotonyl-, succinyl-, propionyl-, butyryl- and sulfur-groups as donors for the modification of sialic acids or other saccharides. Other molecules capable of modifying sialic acids or other saccharides in other forms are also included without limitation.

Sulfur containing compounds or products include inorganic and organic compounds of sulfur. Inorganic compounds of sulfur include but not limited to sulfate (SO$_4^{2-}$), salts of sulfuric acid. Organic compounds or products of sulfur include but not limited to a sulfonate, a sulfonyl, a sulurate, a sulfide, and a sulfur containing amino acid. Sulfur containing compounds or products also include garlic products including but not limited to garlic powder, garlic oil and extract of garlic (Allicin, Allium sativum, Ajoene, etc.).

A saccharide modification molecule (e.g. a sulfide) can be included alone or in combination with sialic acid or other components of the present disclosure.

The amounts or concentrations of a saccharide modification molecule (e.g. a sulfide) in a composition or a product of the present disclosure is from about 0.005 mg/ml to about 900 mg/ml or 0.005 mg/g to about 900 mg/g.

Methionine

An example of sulfur containing amino acid is methionine. Methionine is an amino acid with following characteristics.

Molecular formula: C$_5$H$_{11}$NO$_2$S
Molecular weight: 149.21
Structure: see right.

Methionine can be included alone or in

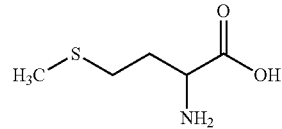

combination with a sialic acid or other components. The amounts or concentrations of methionine in a composition or a product of the present disclosure is from about 0.005 mg/ml to about 900 mg/ml or 0.005 mg/g to about 900 mg/g.

Nutritional or Pharmaceutically Acceptable Salts

Nutritional or pharmaceutically acceptable salts include but not limited to sodium chloride, potassium chloride, sodium citrate, sodium bicarbonate (NaHCO$_3$).

One example is the oral rehydration salts recommended by WHO comprising 3.5 grams of sodium chloride, 1.5 grams of potassium chloride, 2.9 grams of sodium citrate, and 20 grams of glucose, in one liter of water. The amount of potassium citrate or glucose can be adjusted (e.g. reduced).

N-acetylneuraminic acid can be used as an acidic reagent to achieve a desired pH value of an ORS.

Other Therapeutics

Other therapeutics include existing or new therapeutics (known or unknown). Existing or new therapeutics (known or unknown) include but not limited to products consisted of chemicals (e.g. antibiotics), biologicals (e.g. antibodies, proteins and blood products), plants or herbs, and etc. without limitation. Examples of existing or new therapeutics include but not limited to antibiotics or other anti-infective (e.g. interferon or antibodies), anti-inflammation, anti-allergy, anti-autoimmune diseases, anti-oncological diseases, anti-gastrointestinal diseases, anti-respiratory diseases, anti-cardiovascular diseases, anti- neurological diseases, anti-urological diseases, anti-reproductive diseases, anti-endocrine diseases, and any other known or unknown therapeutics without limitation.

Optional Components

Plant Isolates

One optional component of the compositions or products of the present disclosure comprises plant isolates. As used herein, a plant isolate refers to any ingredients or molecules isolated from a pant.

A plant isolate can be included alone or in combination with sialic acid or other components of the present disclosure. The amounts or concentrations of a plant isolate in a composition or a product of the present disclosure is from about 0.1 mg/ml to about 900 mg/ml or 0.1 mg/g to about 900 mg/g.

Inorganic Ions

Another optional component of the compositions or products of the present disclosure comprises the inorganic ions. As used herein, inorganic ions include mineral nutrients that include but not limited to elements boron, copper, manganese, zinc, molybdenum, sulphur, iron, calcium, potassium, nitrate, phosphate, chloride, etc., without limitation.

An inorganic ion can be included in combination with a sialic acid or other components of the present disclosure.

The amounts or concentrations of an inorganic ion in a composition or a product of the present disclosure is from about 0.005 mg/ml to about 500 mg/ml or 0.005 mg/g to about 500 mg/g.

Herbs and Traditional Chinese Herbs

Another optional component of the compositions or products of the present disclosure comprises herbs. As used herein, an herb refers to a plant that is valued for qualities such as medicinal properties, flavor, scent, or the like. In the present disclosure, traditional Chinese herbs include but not limited to all herbs listed in Bencao Gangmu (traditional Chinese: 本草 綱目 simplified Chinese: 本草纲目; pinyin: BěncǎoGāngmù; Wade-Giles: Pen-ts'ao Kang-mu), also known as Compendium of Materia Medica, which is Chinese materia medica work written by Li Shizhen in Ming Dynasty. It is a work epitomizing materia medica (本草) in Ming Dynasty. It lists all the plants, animals, minerals, and other objects that were believed to have medicinal properties.

A herb can be included alone or in combination with a sialic acid or other components of the present disclosure.

The amounts or concentrations of a herb in a composition or a product of the present disclosure is from about 0.1 mg/ml to about 900 mg/ml or 0.1 mg/g to about 900 mg/g.

Others

Other optional components include but not limited to sugar, salt, minerals, vitamins, gelatin and any other necessary components or materials known in the art.

Compositions or Products

In one embodiment the present invention discloses the compositions or products comprise a sialic acid alone or a sialic acid plus at least one of the other major components of the present disclosure. The major components of the present disclosure include but not limited to: 1) a sialic acids including but not limited to N-acetylneuraminic acid, 2-Keto-3-deoxynononic acid, N-Acetylglucosamine, N-Acetylgalactosamine, N-Acetylmannosamine, and N-Glycolylneur-aminic acid; 2) the derivatives or analogs of a sialic acid (e.g. N-Acetylneuraminic acid methyl ester); 3) an other saccharide including but not limited to fructose, glucose, mannose, fucose, xylose, galactose, lactose; 4) a saccharide modifying molecules including but not limited to sulfur-containing amino acids (e.g. methionine and methionine-zinc complex); and 5) nutritional or pharmaceutically acceptable salts include but not limited to sodium chloride, potassium chloride, sodium citrate, or the oral rehydration salts recommended by WHO. The other optional components can be included if necessary.

Wherein, in a composition or a product the amounts or concentrations of a major component (e.g. N-acetylneuraminic acid) are from about 0.005 mg/ml to about 900 mg/ml or about 0.005 mg/g to about 900 mg/g. Wherein the compositions or the products are in a form of a tablet, a capsule (each including timed release and sustained release formulations), a pill, a powder mixture, a granule, an elixir, a tincture, a solution, a suspension, a syrup or a emulsion, a nasal drop or spray, an injectable, an infusion, or a form conjugated to a nano-particle, or other using forms well known to those of ordinary skill in the relevant arts.

Wherein, the compositions are used for making: 1) dietary supplement products to help supporting or enhancing the protective structure or function of gastrointestinal and respiratory tracts of humans and animals; 2) food or feed additives or products comprising the additives for the prevention or treatment of infectious or inflammatory diseases or conditions in particular gastrointestinal respiratory diseases or conditions (e.g. diarrhea and influenza infections); 3) therapeutic products for the prevention and treatment of infectious or inflammatory diseases or conditions in particular gastrointestinal respiratory diseases or conditions (e.g. diarrhea and influenza infections); and 4) oral rehydration salt or oral rehydration solution (ORS) for the prevention and treatment of dehydration due to diarrhea or fever.

One example of the compositions or products containing at least two of the major components of the present disclosure comprise suitable amounts of a sialic acid (e.g. N-acetylneuraminic acid) and a saccharide modifying molecule (e.g. methionine) or a analog of the sialic acid (e.g. N-acetylneuraminic acid methyl ester).

Wherein, a composition or a product comprises about 0.01 mg/mho about 900 mg/ml or 0.01 mg/ml to about 900 mg/g of the sialic acid (e.g. N-acetylneuraminic acid) and about 0.005 mg/ml to about 900 mg/ml or 0.005 mg/g to about 900 mg/g of the saccharide modifying molecule (e.g. methionine) or the analog of a sialic acid (e.g. N-acetylneuraminic acid methyl ester).

Wherein the compositions or the products are in a form of a tablet, a capsule (each including timed release and sustained release formulations), a pill, a powder mixture, a granule, an elixir, a tincture, a solution, a suspension, a syrup or a emulsion, a nasal drop or spray, an injectable, an infusion, or a form conjugated to a nano-particle, or other using forms well known to those of ordinary skill in the relevant arts.

Wherein, the compositions or the products are used as: 1) dietary supplement products to help supporting or enhancing the protective structure or function of gastrointestinal and respiratory tracts of humans and animals; 2) food or feed additives or products comprising the additives for the prevention or treatment of infectious or inflammatory diseases or conditions in particular gastrointestinal respiratory diseases or conditions (e.g. diarrhea and influenza infections);

3) therapeutic products for the prevention and treatment of infectious or inflammatory diseases or conditions in particular gastrointestinal respiratory diseases or conditions (e.g. diarrhea and influenza infections); and 4) oral rehydration salt or oral rehydration solution (ORS) for the prevention and treatment of dehydration due to diarrhea or fever of humans and animals.

Wherein, the humans of the present disclosure include but not limited to males and females, newborns, 1-12 months old infants, 1-18 years old children, adults, old people, pregnant and feeding females.

Wherein, the animals include but not limited to livestock (e.g. pigs or cows), poultry (e.g. chickens), companion animals or pets (e.g. dogs or cats), aquaculture organisms (e.g. fish) and aquatic animals.

In another embodiment the present invention discloses ORS compositions or ORS products for preventing and treating dehydration due to diarrhea or fever of humans and animals as mentioned above. The ORS compositions comprise the combination of suitable amounts of the pharmaceutically acceptable salts and at least one of a sialic acid (e.g. N-acetylneuraminic acid), another saccharide (e.g. galactose or lactose), a saccharide modifying molecule (e.g. methionine), an analog of the sialic acid (e.g. N-acetylneuraminic acid methyl ester), and other optional components of the present disclosure if necessary.

Wherein an ORS product is in a form of a powder mixture or a solution.

Wherein an ORS solution comprises about 0.01 mg/ml to about 5.0 mg/ml of a sialic acid (e.g. the N-acetylneuraminic acid) or another saccharide (e.g. a galactose or a lactose), about 0.005 mg/ml to about 5.0 mg/ml of a saccharide modifying molecule (e.g. methionine) or an analog of the sialic acid (e.g. N-acetylneuraminic acid methyl ester).

Wherein an ORS powder mixture in a total amounts of 20-35 grams for making 1000 ml of ORS solution comprise about 0.01 gram to about 5.0 grams of N-acetylneuraminic acid, about 0.005 gram to 5.0 grams of a glycan modifying molecule (e.g. methionine) or an analog of the sialic acid (e.g. N-acetylneuraminic acid methyl ester).

Wherein, the pharmaceutically acceptable salts comprise 3.5 grams of sodium chloride, 1.5 grams of potassium chloride, 2.9 grams of sodium citrate, and 20 grams of glucose, in one liter of water. The amount of the pharmaceutically acceptable salts can be adjusted (e.g. reduced or increased). The N-acetylneuraminic acid can be used as an acidic reagent to achieve a desired pH value of an ORS.

Methods of Manufacture

In another embodiment the present invention discloses methods of making the compositions or products comprise a sialic acid alone or a sialic acid plus at least one of the other major components of the present disclosure. The major components of the present disclosure include but not limited to: 1) a sialic acids including but not limited to N-acetylneuraminic acid, 2-Keto-3-deoxynononic acid, N-Acetylglucosamine, N-Acetylgalactosamine, N-Acetylmannosamine, and N-Glycolylneur-aminic acid; 2) the derivatives or analogs of a sialic acid (e.g. N-Acetylneuraminic acid methyl ester); 3) an other saccharides including but not limited to fructose, glucose, mannose, fucose, xylose, galactose, lactose; 4) a saccharide modifying molecules including but not limited to sulfur-containing amino acids (e.g. methionine and methionine-zinc complex); and 5) nutritional or pharmaceutically acceptable salts include but not limited to sodium chloride, potassium chloride, sodium citrate, or the oral rehydration salts recommended by WHO. The other optional components can be included if necessary.

One aspect of the methods is consisted of manufacture of a dietary or nutritional supplement or a therapeutic product by combining suitable amounts of a sialic acid (e.g. N-acetylneuraminic acid) alone or the sialic acid plus at least one of the other major components (e.g. a sialic acid or/and methionine or N-acetylneuraminic acid methyl ester) of the present disclosure, and other optional components or materials known in the art if necessary, to form a tablet, a capsule, a pill, a powder mixture, a granule, an elixir, a tincture, a solution, a suspension, a syrup or a emulsion, a nasal drop or spray, an injectable, an infusion, or a form conjugated to a nano-particle, or other using forms well known to those of ordinary skill in the relevant arts.

Wherein, a composition or a product of the present disclosure comprise about 0.01 mg/ml to about 900 mg/ml or 0.01 mg/g to about 900 mg/g of a sialic acid (e.g. a N-acetylneuraminic acid) or another saccharide (e.g. a galactose or a lactose); about 0.005 mg/ml or 0.005 mg/g to about 900 mg/ml or 900 mg/g of a saccharide modifying molecules (e.g. a methionine) or a derivative or an analog of a sialic acid (e.g. a N-acetylneuraminic acid methyl ester); and about 0.1 mg/ml or 0.1 mg/g to about 900 mg/ml or 900 mg/g of a plant isolate or a herb.

In another embodiment the present invention discloses a method of making a food or feed additive by combining suitable amounts of a sialic acid (e.g. N-acetylneuraminic acid) alone or the sialic acid plus at least one of the other major components (e.g. a methionine or a N-acetylneuraminic acid methyl ester) of the present disclosure or/and other optional or necessary materials known in the art to form a powder mixture, a liquid, a paste, a gel, a syrup, a solid and an other form well known to those of ordinary skill in the relevant arts.

Another aspect of the methods is consisted of making a food or a feed comprising adding suitable amounts of a sialic acid (e.g. N-acetylneuraminic acid) alone or the sialic acid plus at least one of the other major components (e.g. a methionine or a N-acetylneuraminic acid methyl ester) of the present disclosure into a food or a feed during the manufacture of the food or the feed, to form a powder mixture, a liquid, a paste, a gel, a syrup, a solid and an other form well known to those of ordinary skill in the relevant arts.

Wherein, a composition or a product of the present disclosure comprise about 0.01 mg/ml to about 900 mg/ml or 0.1 mg/g to about 900 mg/g of a sialic acid (e.g. a N-acetylneuraminic acid) or another saccharide (e.g. a galactose or a lactose); about 0.005 mg/ml to about 900 mg/ml or or 0.005 mg/g to about 900 mg/g of a saccharide modifying molecules (e.g. a methionine) or a derivative or an analog of a sialic acid (e.g. a N-acetylneuraminic acid methyl ester); and about 0.1 mg/ml to about 900 mg/ml or 0.1 mg/g to about 900 mg/g of a plant isolate or a herb.

In another embodiment the present invention discloses a method of making an oral rehydration salt or a rehydration solution (ORS). One aspect of the method comprises the combination of suitable amounts of a sialic acid (e.g. N-acetylneuraminic acid) alone or the sialic acid plus at least one of the other major components (e.g. a methionine or a N-acetylneuraminic acid methyl ester) of the present disclosure and pharmaceutically acceptable salts to form a powder formula or a mixture of an oral rehydration salts.

Another aspect of the method comprises the combination of suitable amounts of a sialic acid (e.g. N-acetylneuraminic acid) alone or the sialic acid plus at least one of the other major components (e.g. a methionine or a N-acetylneuraminic acid methyl ester) of the present disclosure, pharmaceutically acceptable salts and water to form a sterilized oral rehydration solution or a sterilized rehydration solution capable of being used by intravenously administration.

Wherein an ORS solution comprises about 0.01 mg/ml to about 5.0 mg/ml of a sialic acid (e.g. the N-acetylneuraminic acid) or another saccharide (e.g. a galactose or a lactose), about 0.005 mg/ml to about 5.0 mg/ml of a saccharide modifying molecule (e.g. methionine) or an analog of the sialic acid (e.g. N-acetylneuraminic acid methyl ester).

Wherein an ORS powder mixture in a total amounts of 20-35 grams for making 1000 ml of ORS solution comprise about 0.01 gram to about 5.0 grams of N-acetylneuraminic acid, about 0.005 gram to 5.0 grams of a saccharide modifying molecule (e.g. methionine) or an analog of the sialic acid (e.g. N-acetylneuraminic acid methyl ester).

Wherein, the pharmaceutically acceptable salts comprise 3.5 grams of sodium chloride, 1.5 grams of potassium chloride, 2.9 grams of sodium citrate, and 20 grams of glucose, in one liter of water. The amount of the pharmaceutically acceptable salts can be adjusted (e.g. reduced or increased). The N-acetylneuraminic acid can be used as an acidic reagent to achieve a desired pH value of an ORS.

Methods of Uses

In one embodiment the present invention discloses the methods of using the compositions or products comprising suitable amounts of a sialic acid (e.g. N-acetylneuraminic acid) alone or the sialic acid plus at least one of the other major components (e.g. methionine or N-acetylneuraminic acid methyl ester) of the present disclosure as mentioned above for: 1) supporting or enhancing the protective structure or function of gastrointestinal and respiratory tracts; 2) the prevention or treatment of infectious and inflammatory diseases or conditions in particular gastrointestinal respiratory diseases or conditions (e.g. diarrhea, rotavirus and influenza infections); and 3) the prevention and treatment of dehydration due to diarrhea or fever of humans and animals.

More specifically, the infectious and inflammatory diseases or conditions can be caused by viral (e.g. rotavirus or influenza viruses) or bacterial infections, gastroenteritis, nutritional problems or food intolerances, inflammatory or allergy, gastrointestinal and respiratory diseases or conditions (e.g. diarrhea, rotavirus and influenza infections), cancers and any other known or unknown causes.

More specifically, the animals include but not limited to livestocks including but not limited to cows, pigs, horses, sheep or goats, llamas, cattle, donkeys; poultry including but not limited to chickens, ducks, gooses, turkeys and pigeons; companion animals including but not limited to dogs, cats, rodent pets and avian pets.

More specifically, the livestocks include but not limited to males and females, adult animals, newborn animals, infant animals, and other young age animals, pregnant and feeding female animals.

More specifically, the humans include but not limited to males and females, newborns, 1-12 months old infants, 1-18 years old children, adults, old people, pregnant and feeding females.

Wherein, the effective dosages of the compositions or products for the uses as mentioned above are from about 0.01 mg/kg to about 100 mg/kg of a sialic acid (e.g. N-acetylneuraminic acid) or another glaycan (e.g. galactose); about 0.005 mg/kg to about 100 mg/kg of a saccharide modifying molecule (e.g. methionine) or an analog (e.g. or N-acetylneuraminic acid methyl ester) of a sialic acid (e.g. N-acetylneuraminic acid).

In another embodiment the present invention discloses the methods of using the compositions or products comprising suitable amounts of a sialic acid (e.g. N-acetylneuraminic acid) alone or a sialic acid plus at least one of the other major components (e.g. methionine or N-acetylneuraminic acid methyl ester) of the present disclosure as mentioned above, as a dietary supplement, or a food (or feed) supplement or a nutritional supplement, to help support or enhance the protective structure or function of gastrointestinal and respiratory tracts of humans and animals.

One aspect of the methods are consisted of orally administrating suitable amounts of the dietary or nutritional or food or feed supplement to a human or an animal individual at risk of developing weakened or damaged structure or function of gastrointestinal and respiratory tracts. Although the invention mentioned oral formulations, the formulations can be delivered enterally, for example by nasogastric tube, to achieve the same effect.

Another aspect of the methods is consisted of orally administrating the suitable amounts of the dietary or nutritional or food or feed supplement to the pregnant or feeding females with their fetus or sucking babies at risk of developing weakened or damaged structure or function of gastrointestinal and respiratory tracts or infectious and inflammatory diseases.

Wherein, the effective dosages of the compositions or the products for the uses as mentioned above are from about 0.01 mg/kg to about 100 mg/kg of a sialic acid (e.g. N-acetylneuraminic acid) or another glaycan (e.g. galactose); about 0.005 mg/kg to about 100 mg/kg of a saccharide modifying molecule (e.g. methionine) or an analog (e.g. or N-acetylneuraminic acid methyl ester) of a sialic acid (e.g. N-acetylneuraminic acid).

In another embodiment the present invention discloses the methods of using the compositions or products comprising suitable amounts of a sialic acid (e.g. N-acetylneuraminic acid) alone or a sialic acid plus at least one of the other major components (e.g. methionine or N-acetylneuraminic acid methyl ester) of the present disclosure as mentioned above, as a human food additive or a veterinary feed additive or a medicated food additive or a medicated feed additive for the prevention or treatment of infectious and inflammatory diseases or conditions in particular gastrointestinal respiratory diseases or conditions (e.g. diarrhea, rotavirus and influenza infections).

One aspect of the methods is consisted of orally administrating the products as mentioned above to a human or an animal individual at risk of suffering or developing infectious and inflammatory diseases or conditions in particular gastrointestinal respiratory diseases or conditions (e.g. diarrhea, rotavirus and influenza infections).

Another aspect of the methods is consisted of orally administrating the products as mentioned above to the pregnant or feeding females with their fetus or sucking babies at risk of suffering or developing infectious and inflammatory diseases or conditions in particular gastrointestinal respiratory diseases or conditions (e.g. diarrhea, rotavirus and influenza infections).

Wherein, the effective dosages of the compositions or products for the uses as mentioned above are from about 0.01 mg/kg to about 100 mg/kg of a sialic acid (e.g. N-acetylneuraminic acid) or another glaycan (e.g. galactose); about 0.005 mg/kg to about 100 mg/kg of a saccharide modifying molecule (e.g. methionine) or an analog (e.g. or N-acetylneuraminic acid methyl ester) of a sialic acid (e.g. N-acetylneuraminic acid).

In another embodiment the present invention discloses a method of using a pharmaceutical composition or a product comprising suitable amounts of a sialic acid (e.g. N-acetylneuraminic acid) alone or a sialic acid plus at least one of the other major components (e.g. methionine or N-acetylneuraminic acid methyl ester) of the present disclosure or the therapeutic products comprising the pharmaceutical composition as mentioned above to prevent or treat infectious and inflammatory diseases or conditions in particular gastrointestinal respiratory diseases or conditions (e.g. diarrhea, rotavirus and influenza infections).

One aspect of the methods is consisted of administrating the pharmaceutical composition or the therapeutic product to a human or an animal individual at risk of suffering or developing infectious and inflammatory diseases or conditions in particular gastrointestinal respiratory diseases or conditions (e.g. diarrhea, rotavirus and influenza infections); or administrating the pharmaceutical composition or the therapeutic product to the pregnant or feeding females with their fetus or sucking babies at risk of suffering or developing gastrointestinal respiratory diseases or conditions (e.g. diarrhea and influenza infections).

Wherein, the pharmaceutical compositions or the therapeutic products can be provided to a biological organism including the pregnant or feeding females by a variety of routes such as subcutaneous, topical with or without occlusion, oral, intramuscular, intravenous (both bolus and infusion), intraperitoneal, intracavity, or transdermal, inhalant, or other using forms well known to those of ordinary skill in the pharmaceutical arts.

Wherein, the effective dosages of the compositions or products for the uses as mentioned above are from about 0.01 mg/kg to about 100 mg/kg of a sialic acid (e.g. N-acetylneuraminic acid) or another glaycan (e.g. galactose); about 0.005 mg/kg to about 100 mg/kg of a saccharide modifying molecule (e.g. methionine) or an analog (e.g. or N-acetylneuraminic acid methyl ester) of a sialic acid (e.g. N-acetylneuraminic acid).

In another embodiment the present invention discloses the methods of using the ORS compositions or products as mentioned above to prevent and treat dehydration due to diarrhea or fever and rotavirus infection.

One aspect of the methods is consisted of preparing the oral rehydration solution and orally administrating the rehydration solution to a human or an animal individual at risk of suffering or developing dehydration. Another aspect of the methods is consisted of intravenously administrating a sterilized rehydration solution to a human or an animal individual at risk of suffering or developing dehydration.

Another aspect of the methods comprises intravenously administering a sterilized ORS solution to a human or an animal individual at risk of suffering or developing rotavirus infection, or to the pregnant or feeding females with their fetus or sucking babies at risk of suffering or developing rotavirus infection.

Wherein, the effective dosages of the ORS compositions or ORS products for the uses as mentioned above are from about 0.01 mg/kg to about 100 mg/kg of a sialic acid (e.g. N-acetylneuraminic acid) or another glaycan (e.g. galactose); about 0.005 mg/kg to about 100 mg/kg of a saccharide modifying molecule (e.g. methionine) or an analog (e.g. or N-acetylneuraminic acid methyl ester) of a sialic acid (e.g. N-acetylneuraminic acid).

Wherein, the effective dosages of an ORS solution for treating dehydration or rotavirus infection are from about 1 ml/kg to 100 ml/kg.

In another embodiment the present invention discloses the methods of the combination using an existing (e.g. an antibiotic) or new therapeutic (known or unknown) with the compositions or the products comprising a sialic acid (e.g. N-acetylneuraminic acid), or an analog of a sialic acid (e.g. N-acetylneuraminic acid methyl ester) or a sialic acid (e.g. N-acetylneuraminic acid) and an analog of a sialic acid (e.g. N-acetylneuraminic acid methyl ester). The combination uses increase the efficacy or reduce the toxicity or side effects of a therapeutic (e.g. an antibiotic).

One aspect of the methods is consisted of administrating a pharmaceutical composition or a therapeutic product of the present disclosure and another therapeutic product (known or unknown) simultaneously to a human or an animal individual at risk of suffering or developing infectious and inflammatory diseases or conditions in particular gastrointestinal respiratory diseases or conditions (e.g. diarrhea, rotavirus and influenza infections); or to the pregnant or feeding females with their fetus or sucking babies at risk of suffering or developing gastrointestinal respiratory diseases or conditions (e.g. diarrhea rotavirus and influenza infections).

Wherein, the two therapeutic products can be provided to a biological organism including the pregnant or feeding females by a variety of routes such as subcutaneous, topical with or without occlusion, oral, intramuscular, intravenous (both bolus and infusion), intraperitoneal, intracavity, or transdermal, inhalant, or other using forms well known to those of ordinary skill in the pharmaceutical arts.

Wherein, the effective dosages of the compositions or the products of the present disclosure are from 0.01 mg/kg to 100 mg/kg of a sialic acid (e.g. N-acetylneuraminic acid); or 0.005 mg/kg to 100 mg/kg of an analog of a sialic acid (e.g. N-acetylneuraminic acid methyl ester).

Wherein, the effective dosages of the other therapeutics can be increased or reduced (e.g. reduced to ¾ or ¼) when it is used in combination with the sialic acid (e.g. N-acetylneuraminic acid), or the analog of a sialic acid (e.g. N-acetylneuraminic acid methyl ester), or the sialic acid (e.g. N-acetylneuraminic acid) plus the analog of a sialic acid (e.g. N-acetylneuraminic acid methyl ester).

Wherein, existing or new therapeutics (known or unknown) include but not limited to products consisted of chemicals (e.g. antibiotics), biologicals (e.g. antibodies, proteins and blood products), and plants or herbs, and etc. without limitation. Examples of existing or new therapeutics include but not limited to antibiotics or other anti-infective (e.g. interferon or antibodies), anti-inflammation, anti-allergy, anti-autoimmune diseases, anti-oncological diseases, anti-gastrointestinal diseases, anti-respiratory diseases, anti-cardiovascular diseases, anti-neurological diseases, anti-urological diseases, anti-reproductive diseases, anti-endocrine diseases, and any other known or unknown therapeutics without limitation.

The dosage or ratio regimen utilizing all the compositions or products containing the compositions as mentioned above or any other relevant candidates of the compositions according to the present disclosure is selected in accordance with a variety of factors including location and density of the therapeutic target, type, species, age, weight, sex and medical condition of a patient or an animal; the severity of the condition to be treated; the route of administration; the renal and hepatic function of the patient or the animal; and the particular substances thereof employed. Optimal precision in achieving concentrations of the said substances of the present disclosure within the range that yields efficacy without toxicity requires a regimen based on the kinetics of the thereof employed substance availability to target sites. This involves a consideration of the distribution, equilibrium, and elimination of the thereof employed substances of the present disclosure.

The present disclosure also has in one embodiment the objective of providing suitable topical, oral systemic and parenteral nutritional or pharmaceutical compositions for the use in the novel methods of preventing and treating infectious and inflammatory diseases or conditions in particular gastrointestinal respiratory diseases or conditions (e.g. diarrhea, rotavirus and influenza infections) as mentioned above. The compositions or products containing the compositions and/or its relevant candidates and/or its derivatives or any other forms of the compositions identified as the active ingredient can be administered in a wide variety of therapeutic dosage or ratio forms in conventional vehicles for administration. For example, compositions or products of the present disclosure can be administered in such oral dosage forms as tablets, capsules (each including timed release and sustained release formulations), pills, powders, granules, elixirs, tinctures, solutions, suspensions, syrups and emulsions, nasal drops or sprays, an injectable, an infusion, or a form conjugated to a nano-particle, or other using forms well known to those of ordinary skill in the relevant arts.

The Possible Mechanisms of Action

Many microbes bind to mammalian tissues by recognizing specific saccharide ligands. Thus saccharides and saccharide mimetics can be used to block the initial attachment of microbes to cell surface or block their release thus prevent and/or suppress infection (anti-adhesive). Because one of these organisms (e.g. rotavirus) naturally gains access through the gut, the saccharide-based drugs can be delivered directly without the requirement of being distributed systemically. Examples of such applications currently under study include milk oligosaccharides that are believed to be natural antagonists of gastrointestinal infection in infants; and polymers that will block the binding of viruses (Ajit Varli et al.. Essentials of Glycobiology, Second Edition. Cold Spring Harbor Laboratory Press, 2008: pp730).

The present invention discloses using sialic acids as a possible agonist or antagonist by possibly competing with natural viral binding sites of pathogens using sialic acids as their binding sites such as receptors (e.g. rotaviruses or influenza viruses). The application of N-acetylneuraminic acid (Neu5Ac) and N-acetylneuraminic acid methyl ester for the prevention and treatment of rotavirus and influenza infections are described in Exemplification.

In addition, chemical modification of sialic acids can strongly influence all of their properties, in particular ligand functions. For example, O-methylation can hinder or even prevent hydrolysis of the glycosidic bond by sialidase. Other substitution of the hydroxyl groups of sialic acids arise from use of the appropriate donors. For example, S-adenosylmethionine for methylated sialic acid or 5'-phosphosulfate for sulfated molecules (Ajit Varli et al.. Essentials of Glycobiology, Second Edition. Cold Spring Harbor Laboratory Press, 2008: pp207).

One embodiment of the present invention is using methyl- and sulfur-containing molecules as donors for methylation and sulfatation of sialic acids or other saccharides. For example, methionine contains —S—$CH_3$ thus may act as a donor to modify a pathogen binding site (a sialic acid or a saccharide) into methylated and sulfated forms. Such chemical modification of a sialic acid or a saccharide may attenuate even prevent pathogen binding to it.

Numerous other objects, features and advantages of the present disclosure will become readily apparent from the detailed description.

EXEMPLIFICATION

1. Formulations or Products Comprising N-acetylneuraminic Acid and the Methods of Making The major components of the formulations or the products comprise N-acetylneuraminic acid and other optional components (e.g. sugar or salt or ions or vitamins) including oral rehydration salt (ORS) as mentioned above, or other necessary components or materials known in the art. Wherein the oral rehydration salt mixture is consistent of 3.5 grams of sodium chloride, 1.5 grams of potassium citrate, 2.9 grams of sodium citrate, and 20 grams of glucose in a total amount of 27.9 grams and for making 1 liter of solution. The amount of potassium citrate can be reduced. The amounts or concentrations of each component of the ORS mixture are adjustable according to previous arts. Examples of the compositions or products comprising:

1.1 A powder Mixture of N-acetylneuraminic Acid Comprising

A. 1 gram of N-acetylneuraminic acid; and
B. 27.9 grams of ORS mixture.

1.2 A Solution of Sialic Acid Comprising

A. 1 gram of N-acetylneuraminic acid;
B. 27.9 grams of ORS mixture; and
C. 1000 ml (microliter) of sterilized water.

For manufacturing products of a dietary or nutritional supplement, a food or a feed or an food or feed additive, or a therapeutic product containing N-acetylneuraminic acid, combine suitable amounts of N-acetylneuraminic acid, and optional components including the ORS mixture or other necessary materials known in the art, to form a tablet, a capsule, a pill, a powder mixture, a granule, an elixir, a tincture, a solution, a suspension, a syrup or a emulsion, a nasal drop or spray, an injectable, an infusion, or a form conjugated to a nano-particle, or other using forms well known to those of ordinary skill in the relevant arts.

Wherein in a product of a dietary or a nutritional supplement, a food or a feed or an food or feed additive, or a therapeutic, the amounts or concentrations of N-acetylneuraminic acid are from about 0.01 mg/ml to about 900 mg/ml or 0.01 mg/g to about 900 mg/g, the amount of the optional ORS mixture or other nutritionally or pharmaceutically acceptable slats are about 0.1-30 grams and the amounts of sterilized water is from 0.1 ml to 1000 ml.

2. Formulations or Products Comprising N-acetylneuraminic Acid and Methionine and the Methods of Making The major components of the formulations or products comprise N-acetylneuraminic acid, methionine and other optional components including oral rehydration salt (ORS) as described above in the example 1 if necessary. Examples of the compositions or products comprising:

2.1 A powder Mixture of N-acetylneuraminic Acid and Methionine Comprising

A. 1 grain of N-acetylneuraminic acid;
B. 1 gram of methionine; and
C. 27.9 grams of ORS mixture.

2.2 A solution of Sialic Acid and Methionine Comprising

A. 1 gram of N-acetylneuraminic acid;
B. 1 gram of methionine;
C. 27.9 grams of ORS mixture or other ; and
D. 1000 ml (microliter) of sterilized water.

For manufacturing products of a dietary or nutritional supplement, a food or a feed or an food or feed additive, or a therapeutic containing N-acetylneuraminic acid and methionine, combine suitable amounts of N-acetylneuraminic acid, methionine, and optional components including the ORS mixture or other necessary materials known in the art, to form a tablet, a capsule, a pill, a powder mixture, a granule, an elixir, a tincture, a solution, a suspension, a syrup or a emulsion, a nasal drop or spray, an injectable, an infusion, or a form conjugated to a nanoparticle, or other using forms well known to those of ordinary skill in the relevant arts.

Wherein in a product of a dietary or nutritional supplement, a food or a feed or an food or feed additive, or a therapeutic, the amounts or concentrations of N-acetylneuraminic acid are from about 0.01 mg/ml to about 900 mg/ml or 0.01 mg/g to about 900 mg/g, the amounts or concentrations of methionine are from about 0.005 mg/ml to about 900 mg/ml or 0.005 mg/g to about 900 mg/g, the amount of the optional ORS mixture are about 0.1-35 grams and the amounts of sterilized water is from 1 ml to 1000 ml.

3. Formulations or Products Comprising Sialic Acid and N-acetylneuraminic Acid Methyl Ester and the Methods of Making The major components of the formulations or products comprise sialic acid and N-acetylneuraminic acid methyl ester, and optional components including oral rehydration salt (ORS) as described above in the example 1 if necessary. Examples of the composition or products comprising:

3.1 A Powder Mixture of Sialic Acid and N-acetylneuraminic Acid Methyl Ester Comprising A. 1 gram of N-acetylneuraminic acid;
B. 1 gram of N-acetylneuraminic acid methyl ester; and
C. 27.9 grams of ORS mixture.

3.2 A Solution of Sialic Acid and N-Acetylneuraminic Acid Methyl Ester Comprising A. 1 gram of N-acetylneuraminic acid;
B. 1 gram of N-acetylneuraminic acid methyl ester.
C. 27.9 grams of ORS mixture; and
D. 1000 ml (microliter) of sterilized water.

3.3 A Solution of N-acetylneuraminic Acid Methyl Ester (2 mg/ml) Comprising

A. 0.2 gram of N-acetylneuraminic acid methyl ester.
B. 2.79 grams of ORS mixture; and
C. 100 ml (microliter) of sterilized water.

For manufacturing products of a dietary or nutritional supplement, a food or a feed or an food or feed additive, or a therapeutic product containing N-acetylneuraminic acid and N-acetylneuraminic acid methyl ester, combine suitable amounts of N-acetylneuraminic acid, N-acetylneuraminic acid methyl ester, and optional components including oral rehydration salt (ORS) or other necessary materials known in the art, to form a tablet, a capsule, a pill, a powder mixture, a granule, an elixir, a tincture, a solution, a suspension, a syrup or a emulsion, a nasal drop or spray, an injectable, an infusion, or a form conjugated to a nanoparticle, or other using forms well known to those of ordinary skill in the relevant arts.

Wherein in a product of a dietary or nutritional supplement, a food or a feed or an food or feed additive, or a therapeutic, the amounts or concentrations of N-acetylneuraminic acid are from about 0.1 mg/ml to about 900 mg/ml or 0.1 mg/g to about 900 mg/g, the amounts or concentrations of N-acetylneuraminic acid methyl ester are from about 0.05 mg/ml to about 900 mg/ml or 0.05 mg/g to about 900 mg/g, the amount of the optional ORS mixture are about 0.1-30 grams and the amounts of sterilized water is from 1 ml to 1000 ml.

4. Formulations or Products Comprising Sialic Acid, Methionine and N-acetylneuraminic Acid Methyl Ester and the Methods Of Making The major components of the formula mixture comprise sialic acid, methionine, N-acetylneuraminic acid methyl ester, and other optional components including oral rehydration salt (ORS) as described above in the example 1 if necessary. Examples of the composition comprising:

4.1 A Powder Mixture of Sialic Acid, Methionine and N-acetylneuraminic Acid Methyl Ester Comprising A. 1 gram of N-acetylneuraminic acid;
B. 0.5 gram of methionine;
C. 0.5 gram of N-acetylneuraminic acid methyl ester; and
D. 27.9 grams of ORS mixture.

4.2 A Solution of Sialic Acid, Methionine and N-acetylneuraminic Acid Methyl Ester Comprising A. 1 gram of N-acetylneuraminic acid;
B. 0.5 gram of methionine;
C. 0.5 grain of N-acetylneuraminic acid methyl ester;
D. 27.9 grams of ORS mixture; and
E. 1000 ml (microliter) of sterilized water.

For manufacturing products of a dietary or nutritional supplement, a food or a feed or an food or feed additive, or a therapeutic product containing N-acetylneuraminic acid, methionine and N-acetylneuraminic acid methyl ester, combine suitable amounts of N-acetylneuraminic acid, methionine, N-acetylneuraminic acid methyl ester, and optional components including the ORS mixture, or other necessary materials known in the art, to form a tablet, a capsule, a pill, a powder mixture, a granule, an elixir, a tincture, a solution, a suspension, a syrup or a emulsion, a nasal drop or spray, an injectable, an infusion, or a form conjugated to a nanoparticle, or other using forms well known to those of ordinary skill in the relevant arts.

Wherein in a product of a dietary or nutritional supplement, a food or a feed or an food or feed additive, or a therapeutic, the amounts or concentrations of N-acetylneuraminic acid are from about 0.1 mg/ml to about 900 mg/ml or 0.1 mg/g to about 900 mg/g, the amounts or concentrations of methionine or N-acetylneuraminic acid methyl ester are from about 0.05 mg/ml to about 900 mg/ml or 0.05 mg/g to about 900 mg/g, the amount of the optional ORS mixture are about 0.1-30 grams and the amounts of sterilized water is from 1 ml to 1000 ml.

5. Product of ORS Formula Mixtures or Solutions and the Methods of Making

The ORS compositions or products comprise the combination of suitable amounts of the pharmaceutically acceptable ORS salts as described above in the example 1, and at least one of a sialic acid (e.g. N-acetylneuraminic acid), an other saccharides (e.g. galactose or lactose), methionine, N-acetylneuraminic acid methyl ester and other optional components as mentioned above if necessary. Examples of the ORS compositions or products comprising:

5.1 A ORS Powder Mixture With N-acetylneuraminic Acid for Making 1000 ml (Microliter) of ORS Solution Comprising
  A. 100 mg (micrograms) of N-acetylneuraminic acid; and
  B. 27.9 grams of ORS mixture.
5.2 A ORS Powder Mixture with N-acetylneuraminic Acid and Methionine for Making 1000 ml (Microliter) of ORS Solution Comprising
  A. 100 mg (micrograms) of N-acetylneuraminic acid;
  B. 100 mg (micrograms) of methionine; and
  C. 27.9 grams of ORS mixture.
5.3 An ORS Solution with N-acetylneuraminic Acid Comprising
  A. 100 mg (micrograms) of N-acetylneuraminic acid;
  B. 27.9 grams of ORS mixture; and
  C. 1000 ml (microliter) of sterilized water.
5.4 An ORS Solution with N-acetylneuraminic Acid and Methionine Comprising
  A. 100 mg (micrograms) of N-acetylneuraminic acid;
  B. 100 mg (micrograms) of methionine;
  C. 27.9 grams of ORS mixture; and
  D. 1000 ml (microliter) of sterilized water.

Wherein the ORS composition for making 1000 ml of solution comprises about 0.01 mg/ml to about 5 mg/ml of a sialic acid (e.g. the N-acetylneuraminic acid) or an another saccharide (e.g. a galactose or a lactose), about 0.005 mg/ml to about 5 mg/ml of methionine or N-acetylneuraminic acid methyl ester, wherein the ORS composition for a total 20-30 grams of a ORS powder mixture to make 1000 ml of ORS solution comprises about 3.3 mg/g to about 166 mg/g of N-acetylneuraminic acid, about 0.166 mg/g to 166 mg/g of methionine or N-acetylneuraminic acid methyl ester.

For manufacture of products of ORS containing N-acetylneuraminic acid alone or N-acetylneuraminic acid and methionine or N-acetylneuraminic acid methyl ester, combine 20-30 grams or 27.9 grams of the ORS mixture with 0.01-2.0 grams of N-acetylneuraminic acid alone, or with 0.01-2.0 grams of N-acetylneuraminic acid and 0.001-1.0 grams of methionine or N-acetylneuraminic acid methyl ester to form a powder mixture, or to dissolve the mixture in 1000 ml of sterilized water. Optionally in the ORS formulations, the amounts or concentrations of the ORS mixture is adjustable according to previous arts.

6. Methods of Uses 6.1 Prevention and Treatment of Rotavirus Infection with Formulations Preparation of Formulations One package of formula-1.1 mixture consisted of 1.0 gram of N-acetylneuraminic acid and 27.9 grams of oral rehydration salt mixture (as described at 1.1 of the Exemplification) was dissolved in 1000 ml of sterilized water (formula-1.2).

One package of formula-2.1 mixture consisted of 1.0 gram of N-acetylneuraminic acid, 1.0 gram of methionine and 27.9 grams of oral rehydration salt mixture (as described at 2.1 of the Exemplification) was dissolved in 1000 ml of sterilized water (formula-2.2).

One package of formula-3.1 mixture consisted of 1.0 gram of N-acetylneuraminic acid, 1.0 gram of N-acetylneuraminic acid methyl ester and 27.9 grams of oral rehydration salt mixture (as described at 3.1 of the Exemplification) was dissolved in 1000 ml of sterilized water (formula-3.2).

One package of formula-4.1 mixture consisted of 1.0 gram of N-acetylneuraminic acid, 0.5 gram of metnionine, 0.5 gram of N-acetylneuraminic acid methyl ester and 27.9 grams of oral rehydration salt mixture (as described at 4.1 of the Exemplification) was dissolved in 1000 ml of sterilized water (formula-4.2).

One package of formula-5.2 mixture consisted of 0.1 gram of N-acetylneuraminic acid, 0.1 gram of metnionine and 27.9 grams of oral rehydration salt mixture (as described at 5.2 of the Exemplification) was dissolved in 1000 ml of sterilized water (formula-5.4).

One package of a regular oral rehydration salt mixture consisted of 3.5 grams of sodium chloride, 1.5 grams of potassium citrate, 2.9 grams of sodium citrate, and 20 grams of glucose in a total amount of 27.9 grams was dissolved in 1000 ml of sterilized water (ORS alone).

A commercially available antibiotic Enrofloxacin for the treatment of animal diarrhea was prepared as a solution at the concentration of 1 mg/ml with the ORS solution as a vehicle.

The formulations of 1.2, 2.2 and 3.2 were used for the treatment of rotavirus infection. The regular ORS alone and the Enrofloxacin were used as controls. In addition, combination use of formula 1.2 and the Enrofloxacin was also tested for the treatment of rotavirus infection.

Six groups of sucking bulb/c mouse pups with body weight of about 2 grams were inoculated at day 2 after birth (P2) with 20 µl (microliter) of rhesus rotavirus (RRV) at the concentration of $1 \times 10^7$ PFU/ml, followed by being treated once per day at day 3 (P3) via oral administration with 50 µl (microliter) of: 1) the ORS alone (control, n=51); 2) the Enrofloxacin alone (antibiotic control, n=52); 3) the formula-1.2 (n=21); 4) the formula-2.2 (n=50); 5) the formula-3.2 (n=20); and 6) the formula-1.2 and the Enrofloxacin (50 µl+50 µl) (n=21). Mice were kept for 3 weeks after RRV infection.

The course of rotavirus infection is that within week 1 after RRV infection, the pups have diarrhea with watery stools, don't eat well and fail to gain weight as quickly as healthy mice; and some pups with serious illness become jaundiced. By the 2nd week all the mice become jaundiced, don't eat well and fail to gain weight; about 30% of pups with symptoms of infection die and 80% of pups with serious illness die. Viruses are usually cleared and undetectable within one week. An effective result of a treatment was judged by reduced volume and duration of diarrhea, and reduced deaths.

TABLE 1

The results of the efficacy test of mouse pups with rotavirus infection

| Group | n= | Effect* | Not effect | Rate(%)* | OR(effect) | 0.95 CI | P |
|---|---|---|---|---|---|---|---|
| ORS alone | 52 | 1 | 51 | 1.92 | 0.02 | 0.32-31.7 | 0.36 |
| Enrofloxacin | 51 | 3 | 48 | 5.88 | 0.06 | 0.33-28.4 | 0.36 |
| Formula-1.2 | 21 | 15 | 6 | 71.4 | 20.4 | 2.27-183 | 0.002 |

TABLE 1-continued

The results of the efficacy test of mouse pups with rotavirus infection

| Group | n= | Effect* | Not effect | Rate(%)* | OR(effect) | 0.95 CI | P |
|---|---|---|---|---|---|---|---|
| Formula-2.2 | 50 | 46 | 4 | 92.0 | 586 | 63.2-5439 | <0.0001 |
| Formula-3.2 | 20 | 13 | 7 | 65.0 | 27.5 | 3.10-243 | 0.0003 |
| F-1.2 + Enro** | 21 | 19 | 3 | 86.4 | 323 | 31.6-3299 | <0.0001 |

*Efficacy was judged by reduced volume and duration of diarrhea and reduced deaths.
**F-1.2 = Formula-1.2; Enro = Enrofloxacin

TABLE 2

The death rates of the mouse pups with rotavirus infection

| Group | n= | Death | Not died | Rate(%) | OR(risk) | 0.95 CI | P |
|---|---|---|---|---|---|---|---|
| ORS alone | 52 | 15 | 37 | 28.9 | 0.41 | 0.22-1.57 | 0.66 |
| Enrofloxacin | 51 | 12 | 39 | 23.5 | 0.76 | 0.31-1.83 | 0.66 |
| Formula-1.2 | 21 | 3 | 18 | 14.3 | 0.41 | 0.11-1.60 | 0.24 |
| Formula-2.2 | 50 | 1 | 49 | 2.00 | 0.05 | 0.01-0.40 | 0.0001 |
| Formula-3.2 | 20 | 2 | 18 | 10.0 | 0.27 | 0.06-1.33 | 0.13 |
| F-1.2 + Enro* | 21 | 3 | 18 | 14.3 | 0.41 | 0.11-1.60 | 0.24 |

*F-1.2 = Formula-1.2; Enro = Enrofloxacin

The experiment results with statistic analysis are concluded in Table 1 and Table 2. Although all the formulas tested showed efficacy for treating rotavirus infection, formula-2.2 showed the best efficacy (92.0%) (Table 1). The diarrhea of the pups treated with the formular-2.2 was lighter and lasted only 1-2 days; the diarrhea of the pups treated with either ORS alone or Enrofloxacin was serious and lasted 3-4 days (Table 1). In addition, only one pups treated with the formula-2.2 died while 15 and 12 pups of the ORS- or enrofloxaci-treated pups died (Table 2). The data showed that formula-2.2 significantly reduced the death rate of rotavirus infection. Further, the combination use of formula-1.2 comprising N-acetylneuraminic acid and Enrofloxacin significantly increased the efficacy or reduced the toxicity of the antibiotic.

The effective dosages of the formulas for the treatment of rotavirus infection of other organisms including humans are from 0.1 mg/kg to 100 mg/kg of N-acetylneuraminic acid or methionine or N-acetylneuraminic acid methyl ester. The effective dosages of Enrofloxacin can be reduced to ¼-¾ of the amounts instructed by the manufacture when it is used in combination with N-acetylneuraminic acid.

6.2. Treatment of Piglet Diarrhea with Formulations

Diarrhea is a common disorder with sucking or weaning piglets. Viral or bacterial infections are common causes of piglet diarrhea. Piglets with viral diarrhea usually have yellow watery stools and piglets with bacterial diarrhea usually have gray stools. Sometimes, yellow diarrhea is accompanied with vomiting showing the characteristic of infective gastroenteritis. Often, piglet diarrhea or infective gastroenteritis is caused by mixed infection of viruses and bacteria. Piglets younger than one week could have a serious viral diarrhea or infective gastroenteritis with high death rates from about 70% to over 90%.

The formulations of 1.2, 2.2, 3.2 and 4.2 as prepared above in 6.1 were used for the treatment of diarrhea piglets at ages 1-5 days. The ORS alone and the Enrofloxacin were used as controls. In addition, combination of formula 1.2 and Enrofloxacin was also used for the treatment of piglet diarrhea.

Seven groups of sucking piglets with yellow watery diarrhea or infective gastroenteritis at ages of 1-5 days were treated once per day via oral administration or muscular injection with: 1) 1 ml/kg of body weight of ORS alone (control group, n=50); 2) Enrofloxacin according to manufacture's instruction (antibiotic control, n=69); 3) 1 ml/kg of body weight of the formula-1.2 (n=49); 4) 1 ml/kg of body weight of the formula-2.2 (n=82); 5) 1 ml/kg of body weight of the formula-3.2 (n=55); 6) 1 ml/kg of body weight of the formula-3.2 (n=51); and 7) 1 ml/kg of body weight of the formula-1.2 plus Enrofloxacin (n=32).

76 out of 82 (92.7%) and 46 out 51 (90.2%) of piglets treated with formula-2.2 and formula-4.2 stopped diarrhea within 24 hours after one dose treatment; while majority of piglets treated with Enrofloxacin stopped diarrhea at day 4-5 after treatment with one dose treatment every day. Over 80% of piglets treated with formula-1.2 or formula-3.2 stopped diarrhea within 24-48 hours after 1-2 dose treatment. In addition, the combination use of formula-1.2 comprising N-acetylneuraminic acid and Enrofloxacin significantly increased the efficacy or reduced the toxicity of the antibiotic. The death rates of piglets with different treatments of formulations are concluded in Table 3.

TABLE 3

The death rates of diarrhea piglets with different treatment of fomulations

| Group | n= | Death | No death | Rate(%)* | OR(risk) | 0.95 CI | P |
|---|---|---|---|---|---|---|---|
| ORS alone | 50 | 46 | 4 | 92.0 | 5.03 | 1.60-15.8 | 0.002 |
| Enrofloxacin | 69 | 48 | 21 | 69.6 | 0.19 | 0.06-0.62 | 0.002 |
| Formula-1.2 | 49 | 2 | 47 | 4.08 | 0.004 | 0.0006-0.02 | <0.0001 |
| Formula-2.2 | 82 | 1 | 81 | 2.23 | 0.001 | 0.0001-0.01 | <0.0001 |
| Formula-3.2 | 55 | 2 | 53 | 3.64 | 0.003 | 0.0006-0.02 | <0.0001 |
| Formula-4.2 | 51 | 1 | 50 | 1.96 | 0.007 | 0.00-0.06 | <0.0001 |
| F-1.2 + Enro** | 32 | 2 | 30 | 5.88 | 0.005 | 0.0009-0.03 | <0.0001 |

*death rate.
**F-1.2 = Formula-1.2; Euro = Enrofloxacin

The effective dosages of the formulas for the treatment of piglet diarrhea and infective gastroenteritis are from 0.1 mg/kg to 100 mg/kg of N-acetylneuraminic acid or methionine or N-acetylneuraminic acid methyl ester. The effective dosages of Enrofloxacin can be reduced to ¼-¾ of the amounts instructed by the manufacture when it is used in combination with N-acetylneuraminic acid.

6.3. Treatment of Piglet Diarrhea with Formulations

The formula-2.2 as prepared above in 6.1 was used for the treatment of diarrhea piglets at ages 5-40 days.

Two groups of sucking or weaning piglets with various diarrheas or infective gastroenteritis at ages of 5-40 days were treated once per day via oral administration with: 1) Enrofloxacin according to manufacture's instruction (antibiotic group, n=139); and 2) 1 ml/kg of body weight of the formula-2.2 (n=262).

Over 90% of piglets treated with formula-2.2 stopped diarrhea within 24 hours after one dose treatment; while majority of piglets treated with Enrofloxacin stopped diarrhea at day 4-5 after 4-5 dose treatment (one dose every day). The results are concluded in Table 4. The data indicated that the formula-2.2 comprising N-acetylneuraminic acid and methionine is effective for the treatment of various diarrheas caused by viruses and bacteria.

TABLE 4

The results of the efficacy tests with formula-2.2 for the diarrhea piglets

| Group | n= | Early Rec* | Later Rec** | Rate (%) | OR | 0.95 CI | P |
|---|---|---|---|---|---|---|---|
| Enrofloxacin | 139 | 3 | 136 | 2.16 | 0.001 | 0.00-0.008 | <0.0001 |
| Formula-2.2 | 262 | 259 | 3 | 98.9 | 3971 | 791-19939 | <0.0001 |

*Recovered within 48 hours (Rec means recovery);
**recovered after 48 hours.

The effective dosages of the formula-1.2 for the treatment of piglet with various diarrhea and infective gastroenteritis are from 0.1 mg/kg to 100 mg/kg of N-acetylneuraminic acid or methionine.

6.4. Prevention of Gastrointestinal and Respiratory Diseases of Piglet with Formulations The formulations of 1.2, 2.2, 3.2 and 4.2 as prepared above in 6.1 were used at age of day 5 for the prevention of piglet diarrhea. The ORS alone was used as control.

Five groups of healthy sucking piglets at age of day 5 were treated once per day via oral administration with: 1) 1 ml/kg of body weight of ORS alone (control group, n=126); 2) 1 ml/kg of body weight of the formula-1.2 (n=19); 3) 1 ml/kg of body weight of the formula-2.2 (n=160); 4) 1 ml/kg of body weight of the formula-3.2 (n=18); and 5) 1 ml/kg of body weight of the formula-4.2 (n=46). The piglets were observed for the symptoms of diarrhea and other diseases up to day 40.

During the period of observation, all the formulas tested showed significant efficacies for the prevention of piglet diarrhea compared to the ORS control (Table 5). The piglets treated with formula-2.2 or formula-4.2 showed the lowest diarrhea frequencies (11.3% and 8.70%, Table 5). In addition, the diarrhea of the piglets treated with the formulations was lighter and lasted only 1-2 days. The diarrhea of the piglets treated with ORS alone was serious and lasted 3-4 days. The results are concluded in Table 5.

During the period of observation, an outbreak of foot and mouth disease virus (FMDV) infection occurred. The piglets treated with formula-4.2 did not infected with the FMDV; the other piglets treated with formula-2.2, formula-3.2 were infected with significantly reduced frequencies (about 20%) without any deaths compared to the piglets without treating with any formulas (99%). In addition, some of the piglets without treating with any formulas infected with porcine circovirus (PCV) during the period of observation while none of the piglets treated with formulas were infected with PCV. Further, during the period of observation, majority of piglets treated with the formulations did not show the symptoms of other diseases such as diarrhea, gastroenteritis, asthma, respiratory infections or other disorders. The data indicated that the formulations of the present invention are effective for the prevention of various gastrointestinal and respiratory infections and other diseases including but not limited to diarrhea caused by viruses or bacteria, infective gastroenteritis, asthma, respiratory syndrome, other viral infections such as FMDV and PCV infections.

TABLE 5

The diarrhea frequencies of newborn piglets with preventative treatment of formula

| Group | n= | Diarrhea | Healthy | Rate (%) | OR (risk) | 0.95 CI | P |
|---|---|---|---|---|---|---|---|
| ORS alone | 126 | 88 | 38 | 69.8 | 33.1 | 16.9-57.4 | <0.0001 |
| Formula-1.2 | 19 | 8 | 11 | 42.1 | 0.31 | 0.12-0.84 | 0.03 |
| Formula-2.2 | 160 | 18 | 142 | 11.3 | 0.55 | 0.03-0.10 | <0.0001 |
| Formula-3.2 | 18 | 6 | 12 | 33.3 | 0.22 | 0.08-0.62 | 0.005 |
| Formula-4.2 | 46 | 4 | 42 | 8.70 | 0.04 | 0.01-0.12 | <0.0001 |

The effective dosages of the formulas for the prevention of diarrhea, infective gastroenteritis, asthma, respiratory syndrome, respiratory infections, other viral infections such as FMDV and PCV infections, or other disorders are from 0.1 mg/kg to 100 mg/kg of N-acetylneuraminic acid or methionine or N-acetylneuraminic acid methyl ester.

6.5 Treatment of Human Diarrhea with Formula-5.4

The formula-2.2 and the ORS formula-5.4 comprising 0.1 mg/ml of N-acetylneuraminic acid and methionine as prepared above in 6.1 was used for the treatment of human diarrhea and dehydration.

Six adult individuals suffered from acute watery diarrhea with or without dehydration were treated once per day via oral administration with formula-2.2 at the dose of 0.5-1 ml/kg of body weight for the subjects with diarrhea alone; or the ORS formula-5.4 at the dose of 300-500 ml each time (2-4 doses per day) for the subjects with diarrhea and dehydration. Five out of six (5/6, 83.3%) of the subjects stopped diarrhea within 1-2 hours after one dose of the treatment with formula-2.2 or formula-5.4. The symptoms of dehydration were improved within 12 hours. Compared to the subjects treated with Ciprofloxacin, None of the formulations showed any side effects such as nausea, headache, stomach cramps, dizziness etc.

The effective dosages of the formulas for the treatment of human diarrhea and dehydration are from 0. 1 mg/kg to 100 mg/kg of N-acetylneuraminic acid or methionine.

6.5 Treatment of Diarrhea of Companion Animals with Formula-2.2

Two groups of dogs suffered from acute diarrhea with the symptoms of vomiting, depression, dehydration, listlessness, an increased frequency of diarrhea were treated once per day via oral administration or intramuscular injection with: 1) Cephradine according to manufacture's instruction (antibiotic group, n=15); and 2) 1.5 ml/kg of body weight of the formula-2.2 (n=10). Eight out ten (8/10, 80%) of the dogs stopped diarrhea after one dose of the treatment with formula-2.2. The symptoms of vomiting, depression, dehydration, listlessness, an increased frequency of diarrhea were significantly improved within 24 hours. The results are listed in Table 6.

TABLE 6

The results of the efficacy tests with formula-2.2 for the diarrhea dogs

| Group | n= | Early Rec* | Later Rec** | Rate (%) | OR | 0.95 CI | P |
|---|---|---|---|---|---|---|---|
| Cephradine | 15 | 1 | 14 | 6.67 | 0.02 | 0.001-0.23 | 0.0003 |
| Formula-2.2 | 10 | 8 | 2 | 80.0 | 56 | 4.40-719 | 0.0003 |

*Recovered within 24 hours (Rec means recovery);
**recovered after 24 hours.

The effective dosages of the formulas for the treatment of diarrhea, dehydration and gastroenteritis of companion animals are from 0.1 mg/kg to 100 mg/kg of either N-acetylneuraminic acid or methionine. The dose amount of the antibiotic of Cephradine can be reduced to ¼-¾ of the dosage recommended by manufactures when it is used in combination with N-acetylneuraminic acid or N-acetylneuraminic acid plus N-acetylneuraminic acid methyl ester.

6.6 Treatment of Mouse Influenza Infection with Formulas

The formulations of 1.2, 3.2 and 3.3 as prepared above in 6.1 and 3.3 were used for the treatment of mouse pups infected with an influenza virus of A/PR/8/34(H1N1). The ORS alone and a commercially available antibiotic product, Tamiflu (prepared as a solution of 2 mg/ml) were used as controls. In addition, combination use of formula 1.2 or formula 3.2 and the Tamiflu was also used for the treatment of influenza infection of mice.

Seven groups of newborn bulb/c pups were inoculated at day 5 (P5) via oral and nasal administration of 30 microliter of the A/PR/8/34(H1N1) influenza virus strain (titer: 1:512, diluted 100 times with saline); and were treated at day 2, 3, 4 and 5 after the viral infection via intraperitoneal injection with 1) 100 microliter of ORS alone (n=30); 2) 100 microliter of Tamiflu (2 mg/ml) (n=30); 3) 100 microliter of formula-3.2 (n=30); 4) 100 microliter of formula-3.3 (2mg/ml) (n=30); 5) 100 microliter of formula-1.2 plus 100 microliter of Tamiflu (2 mg/ml) (n=21); and 6) 100 microliter of formula-3.2 plus 50 microliter of Tamiflu (2 mg/ml) (n=21). Mice were kept for 7 days after infection.

The results are listed in Table 7. 26/30 (86.7%) of mice treated with ORS alone and 70% of the mice treated with Tamiflu died during the course of the influenza infection. The death rates of the pups treated with formula-3.2 and formula-3.3 were reduced to 23.3% and 40% respectively. In addition, the combination use of Tamiflu and N-acetylneuraminic acid or N-acetylneuraminic and N-acetylneuraminic acid methyl ester significantly increased the efficacy or reduced the toxicity of the antibiotic compared to the efficacy of Tamiflu alone.

TABLE 7

The results of efficacy test of formulas for influenza infection of mice

| Treatment with | n= | Death | *Rate (%) | Odds Ratio | 95% CI | P value |
|---|---|---|---|---|---|---|
| ORS alone | 30 | 26 | 86.7 | 2.79 | 0.75-10.3 | 0.21 |
| Tamiflu | 30 | 21 | 70.0 | 0.36 | 0.10-1.33 | 0.21 |

TABLE 7-continued

The results of efficacy test of formulas for influenza infection of mice

| Treatment with | n= | Death | *Rate (%) | Odds Ratio | 95% CI | P value |
|---|---|---|---|---|---|---|
| Formula-3.2 | 30 | 7 | 23.3 | 0.05 | 0.01-0.18 | <.0001 |
| Formula-3.3 | 10 | 4 | 40.0 | 0.10 | 0.02-0.53 | 0.007 |
| Formula-1.2 + Tamiflu | 21 | 10 | 47.6 | 0.14 | 0.04-0.54 | 0.004 |
| Formula-3.2 + Tamiflu | 22 | 8 | 36.3 | 0.09 | 0.02-0.34 | 0.0003 |

*Death rate.

The effective dosages of the formulas for the treatment of influenza infection are from about 0.1 mg/kg to 100 mg/kg of N-acetylneuraminic acid or N-acetylneuraminic acid methyl ester. The dose amount of the antibiotic (Tamiflu) can be reduced to ¼-¾ of the dosage recommended by manufactures when it is used in combination with N-acetylneuraminic acid or N-acetylneuraminic acid plus N-acetylneuraminic acid methyl ester.

6.7 Treatment of Respiratory Infections or Disorders of Piglets with Formulas

The formulations of 1.2 and 3.2 as prepared above in 6.1 were used for the prevention and treatment of respiratory infections or disorders of piglets. The ORS alone and a commercially available antibiotic product, Timicosin were used as controls. In addition, combination of formula 3.2 and Timicosin was used for the treatment of respiratory infections or disorders of piglets.

Weaning piglets (10~15 kg, aged 5-7 weeks) suffered from respiratory infections accompanied with the respiratory syndrome characterized by asthma-like symptoms (difficulty with breath). The sick piglets were treated separately once a day via oral administration or intramuscular injection with 1) Tilmicosin according to manufacture's instructions (n=39); 2) 1 ml/kg of body weight of the formula-3.2 (n=36); and 3) Tilmicosin and 1 ml/kg of body weight of the formula-3.2 (n=41).

Majority (37/41, 90.2%) of the piglets treated with the formula-3.2 or Tilmicosin plus the formula-3.2 recovered at day four (3 doses); while it took 4-5 doses for the piglets treated with Tilmicosin alone getting recovered. In addition, the death rate of the piglets treated with the formula-3.2 plus Tilmicosin (9.76%) was significantly lower compared with the death rate of the piglets treated with Tilmicosin alone (28.2%) (Table 8).

TABLE 8

The death frequenciess of the piglets with respiratory syndrome (asthma)

| Treated with | n= | Death | Rate (%) | Odds Ratio | 95% CI | P value |
|---|---|---|---|---|---|---|
| Tilmicosin | 39 | 11 | 28.2 | 3.63 | 1.05-12.6 | 0.05 |
| Formula-3.2 | 36 | 4 | 11.1 | 0.32 | 0.09-1.11 | 0.08 |
| F-3.2* + Tilmicosin | 41 | 4 | 9.76 | 0.28 | 0.08-0.96 | 0.05 |

*F-3.2 = Formula-3.2

The effective dosages of the formulas for the treatment of respiratory infections, the respiratory syndrome, asthma, and other respiratory disorders of piglets are from about 0.1 mg/kg to about 100 mg/kg of N-acetylneuraminic acid or N-acetylneuraminic acid methyl ester. The dose amount of the antibiotic of Timicosin can be reduced to ¼-¾ of the dosage recommended by manufactures when it is used in combination with N-acetylneuraminic acid or N-acetylneuraminic acid plus N-acetylneuraminic acid methyl ester.

6.8 Treatment of Respiratory Infections or Disorders of Companion Animals with Formulas The formula-3.2 as prepared above in 6.1 was used via oral administration for the prevention or treatment of respiratory infections or disorders of dogs.

Two groups of dogs suffered from respiratory infections with the symptoms of runny nose, coughing, chills, fever and weakness/fatigue (etc.) were treated once per day via oral administration or intramuscular injection with: 1) Tulathromycin according to manufacture's instruction (antibiotic group, n=6); 2) 1.5 ml/kg of body weight of the formula-3.2 (n =6); and 3) Tulathromycin and 1.5 ml/kg of body weight of the formula-3.2 (n=9).

Majority (13/15, 86.7%) of the dogs treated with either the formula-3.2 or tulathromycin plus the formula-3.2 recovered at day two or three (2-3 doses); while it took 4-7 doses for the dogs treated with tulathromycin alone getting recovered (Table 9).

TABLE 9

The results of the efficacy tests with formula-3.2 for dogs with respiratory infections

| Group | n= | Early Rec* | Later Rec | Rate (%) | OR | 0.95 CI | P |
|---|---|---|---|---|---|---|---|
| Tulathromycin | 6 | 1 | 5 | 16.7 | 0.04 | 0.002-0.83 | 0.08 |
| Formula-3.2 | 6 | 5 | 1 | 83.3 | 25.0 | 1.20-521 | 0.08 |
| F-3.2 + Tula** | 9 | 8 | 1 | 88.9 | 40.0 | 2.0-794 | 0.01 |

*Recovered within 48-72 hours (Rec means recovery).
**F-3.2 = Formula-3.2; Tula = Tulathromycin.

The effective dosages of the formulas for the treatment of respiratory infections or disorders of companion animals are from about 0.1 mg/kg to 100 mg/kg of N-acetylneuraminic acid or N-acetylneuraminic acid methyl ester. The dose amount of the antibiotic of tulathromycin can be reduced to ¼-¾ of the dosage recommended by manufactures when it is used in combination with N-acetylneuraminic acid or N-acetylneuraminic acid plus N-acetylneuraminic acid methyl ester.

6.9 Treatment of Respiratory Infections Including Influenza of Humans with Formulas The formula-3.2 as prepared above in 6.1 was used once a day via oral administration for the treatment of eleven human subjects with respiratory infections including influenza infections with the symptoms of coughing, chills, fever, sore throat, runny nose, muscle pains, headache (often severe), weakness/fatigue, etc. The dose was 0.5-1.0 mg/kg body weight.

The symptoms of 10/11 (91%) of the subjected treated with formula-3.2 were significantly reduced, and all the subjects recovered within three days after starting the treatment.

The effective dosages of the formulas for the treatment of respiratory infections including influenza infections of humans are from about 0.1 mg/kg to 100 mg/kg of N-acetylneuraminic acid or N-acetylneuraminic acid methyl ester.

6.10 Prevention and Treatment of Inflammatory Disorders with Formulations

The formula-3.2 as prepared above in 6.1 was used via oral administration for the prevention or treatment of human pollen allergy (3), rhinitis (n=5), sinusitis (n=2), arthritis (n=3), essential tremor (n=2) and Parkinson's disease (n=1).

The three subjects suffered from pollen allergy every year were treated once a day by nasal (1-2 ml) and oral administration (20-50 ml) of the formula-3.2 during the outbreak season. No significant symptoms of pollen allergy were observed with the three subjects.

The five subjects with rhinitis and the two subjects with sinusitis were treated once a day by nasal (1-2 ml) and oral administration (20-50 ml) of the formula-3.2. About 70% of the symptoms of the rhinitis and sinusitis were significantly reduced within two hours of the treatment.

The three subject with arthritis were treated once a day by oral administration (20-50 ml) of the formula-3.2. Significant pain relief was observed within two hours of the treatment.

The two subjects with essential tremor were treated once a day by oral administration (20-50 ml) of the formula-3.2 or the formula-1.2 or 10-25 ml of the formula-3.3. The trembling width and the frequencies were reduced about 50% after 2-3 days treatment with each the formula respectively.

The subject with Parkinson's disease was treated once a day by oral administration (20-50 ml) of the formula-3.2. The trembling width and the frequencies were reduced about 50% after 2-3 days treatment with the formula.

Taken together, the data indicated that the formulas comprising N-acetylneuraminic acid or N-acetylneuraminic acid methyl ester or N-acetylneuraminic acid and N-acetylneuraminic acid methyl ester have broad effects on the inflammatory disorders, allergy and autoimmune diseases include but not limited to pollen allergy, rhinitis, sinusitis, arthritis, essential tremor and Parkinson's disease.

In addition, combination use of N-acetylneuraminic acid or N-acetylneuraminic acid methyl ester or N-acetylneuraminic acid and N-acetylneuraminic acid methyl ester with other existing therapeutic products for those disorders reduced the adverse reactions or toxicity and increase the efficacy of those products.

The effective dosages of the formulas for the treatment of human inflammatory disorders or conditions are from about 0.1 mg/kg to 100 mg/kg of N-acetylneuraminic acid or N-acetylneuraminic acid methyl ester.

6.11 Prevention and Treatment of Side Effects of Interferon with Formula-1.2

Three HCV-infected human subjects have the history of interruption of interferon therapy due to the side effects of interferon. The side effects of interferon included nausea, vomiting and upset stomach along with diarrhea or constipation, headache and drowsiness, thinning of the hair, depression, excessive sleepiness and confusion, etc.

The formula-1.2 as prepared above in 6.1 was used once a day via oral administration to the three HCV-infected subjects to prevent and treat the side effects of interferon at the time of their resuming interferon therapy. The doses were 0.5-1.0 mg/kg body weight.

The symptoms of the interferon side effects of the three subjects treated with formula-1.2 were significantly reduced, and all the subjects finished the entire course of the interferon therapy. The data indicated that N-acetylneuraminic acid can reduce the side effects of interferon.

The effective dosages of N-acetylneuraminic acid for the treatment of side effects of a therapeutic are from about 0.1 mg/kg to 100 mg/kg.

Other embodiments besides the above may be articulated as well. The terms and expressions therefore serve only to describe the disclosure by example only and not to limit the disclosure. It is expected that others will perceive differences, which while differing from the foregoing, do not depart from the spirit and scope of the disclosure herein described and claimed. All patents, patent publications, and other references cited herein are incorporated herein by reference in their entirety.

Additional Exemplification 6.12 Prevention of gastrointestinal and respiratory diseases of weaning piglets with formulations as feed additives 6.12.1. Formulations or products comprising sialic acid and N-acetylglucosamine The major components of the formula mixture comprise sialic acid and N-acetylglucosamine, and other optional components including oral rehydration salt (ORS) as described above in the example 1 if necessary. Examples of the composition or products comprising:

6.12.1-1 A Powder Mixture Of Sialic Acid and N-acetylglucosarnine Comprising
   A. 0.5-5 grams of N-acetylneuraminic acid;
   B. 0.1-5 grams of N-acetylglucosamine; and
   C. 15-30 grams of ORS mixture.

6.12.1-2 A Solution of Sialic Acid and N-acetylglucosamine Comprising
   A. 0.5-5 grams of N-acetylneuraminic acid;
   B. 0.1-5 grams of N-acetylglucosamine;
   C. 15-30 grams of ORS mixture; and
   D. 1000 ml (microliter) of sterilized water.

6.12.1-3 A Powder Mixture of Sialic Acid and N-acetylglucosamine Comprising
   A. 1-20 grams of N-acetylneuraminic acid;
   B. 0.1-20 grams of N-acetylglucosamine; and
   C. 50-500 grams of ORS mixture.

6.12.1-4 A Powder Mixture of Sialic Acid and Methionine Comprising
   A. 1-20 grams of N-acetylneuraminic acid;
   B. 0.1-20 grams of methionine; and
   C. 50-500 grams of ORS mixture.

6.12.2. Methods of Making

Wherein the N-Acetyl glucosamine is a sialic acid with following characteristics.

Molecular formula: $C_8H_{15}NO_6$
Molecular weight: 221.21
Structure: shown at right For manufacturing products of a dietary or nutritional supplement, a food or a feed or a food or feed additive, or a

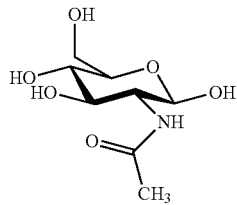

therapeutic product containing N-acetyl-neuraminic acid alone, adding suitable amounts of N-acetylneuraminic acid to the product and optional components including the ORS mixture, or other necessary materials known in the art, to form a tablet, a capsule, a pill, a powder mixture, a granule, an elixir, a tincture, a solution, a suspension, a syrup or a emulsion, a nasal drop or spray, an injectable, an infusion, or a form conjugated to a nano-particle, or other using forms well known to those of ordinary skill in the relevant arts.

For manufacturing products of a dietary or nutritional supplement, a food or a feed or a medicated food additive or medicated feed additive, or a therapeutic product containing N-acetyl-neuraminic acid and N-acetyl glucosamine or methionine, combine suitable amounts of N-acetylneuraminic acid, N-acetylglucosamine or methionine, and optional components including the ORS mixture, or other necessary materials known in the art, to form a tablet, a capsule, a pill, a powder mixture, a granule, an elixir, a tincture, a solution, a suspension, a syrup or a emulsion, a nasal drop or spray, an injectable, an infusion, or a form conjugated to a nano-particle, or other using forms well known to those of ordinary skill in the relevant arts.

Wherein in a product of a dietary or nutritional supplement, a food or a feed or a medicated food additive or medicated feed additive, or a therapeutic, the amounts or concentrations of N-acetylneuraminic acid are from about 0.1 mg/ml to about 900 mg/ml or 0.01 mg/g to about 900 mg/g, the amounts or concentrations of N-acetylglucosamine or methionine are from about 0.05 mg/ml to about 900 mg/ml or 0.05 mg/g to about 900 mg/g, the amount of the ORS mixture are about 1.0-580 grams in a pack of powder mixture of about 500-600 grams.

6.12.2. Methods of Using

The formula-6.12.1-3 comprising N-acetylneuraminic acid and N-acetyl glucosamine and the formula-6.12.1-4 comprising N-acetylneuraminic acid and methionine as mentioned above were tested with weaning piglets at age of 4-5 weeks for the prevention of diarrhea of weaning piglets.

Making Feed with Formulas
   a. Feed used: Premix nursery feed without antibiotics (made in Belgium and Switzerland).
   b. Formula-6.12.1-3: mixing 4 grams of N-acetylneuraminic acid, 4 grams of N-acetylglucosamine and 250 grams of rehydration salt (vehicle) to form a powder mixture (about 258 g/pack).
   c. Formula-6.12.1-4: mixing 4 grams of N-acetylneuraminic acid, 4 grams of methionine and 250 grams of rehydration salt (vehicle) to form a powder mixture (about 258 g/pack).
   d. Feed with formulas: adding one pack (~258 g) of the powder mixture of formula-6.12.1-3 or formula-6.12.1-4 into 500 kg of the premix nursery feed, and mix thoroughly. The final concentration of the formula in the nursery feed is about 8 mg/kg of each of N-acetylneuraminic acid and N-acetylglucosamine (formula-6.12.1-3) or methionine (formula-6.12.1-4).
   e. Control feed: adding one pack of ORS (~250 g) into 500 kg of the premix nursery feed, and mix thoroughly. This feed without any formulas was used as control.

Method of Using

Prevention of Diarrhea and Other Diseases of Weaning Piglets

Weaning pigs: aged at 4-5 weeks and at 1-5 day of feeding with nursery feed.

Test group-1: 175 of weaning piglets, fed with nursery feed with formula-6.12.1-3 as mentioned above.

Test group-2: 108 of weaning piglets, fed with nursery feed with formula-6.12.1-4 as mentioned above.

Control group: 256 of piglets, fed with nursery feed with ORS alone as mentioned above.

The nursery feeds were given from 1-5 days of the beginning of the nursery feeding. The total feeding days with the nursery feeds were 5-10 days.

The Observed Results
   The piglets treated with the feed with either formula-6.12.1-3 or formula-6.12.1-4 looked healthy with pink skin and shining fur compared to the pigs of the control group. The diarrhea rate of the weaning piglets of the control group was 53.9%; the diarrhea rates of the weaning piglets of the test group-1 and group-2 were 5.71% and 5.56% separately (Table 10). The diarrhea of the two test group piglets was lighter (not water-like diarrhea) compared to the diarrhea of control group piglets (water-like diarrhea). The death rate of the control group piglets was 15.6%. The death rates of the piglets of the two test groups were only 0.06% (group-1) and 1.85% (group-2) separately (Table 11).

The diarrhea piglets of control group were treated with antibiotic (ofloxacin). The piglets treated with antibiotic grew slowly, looks smaller and not healthy. The diarrhea piglets of the test groups were not treated and they did not lose body weight significantly and looked in a good healthy status.

TABLE 10

The diarrhea rates of weaning piglets with formula-6.12.1-3 (methionine)

| Group | N= | Diarrhea | No diarrhea | Rate (%) | OR (risk) | 0.95 CI | p** |
|---|---|---|---|---|---|---|---|
| *F-6.12.1-3 | 175 | 10 | 165 | 5.71 | 0.05 | 0.03-1.03 | <.0001 |
| F-6.12.1-4 | 108 | 6 | 102 | 5.56 | 0.05 | 0.02-0.13 | <.0001 |
| Control | 256 | 138 | 118 | 53.9 | 19.3 | 9.74-38.2 | <.0001 |

*F = Formula;
**Chi-Square, Pearson

TABLE 11

The death rates of weaning piglets with formula-6.12.1-3

| Group | N= | Death | No death | Rate (%) | OR (risk) | 0.95 CI | p** |
|---|---|---|---|---|---|---|---|
| *F-6.12.1-3 | 175 | 1 | 174 | 0.06 | 0.03 | .004-0.28 | <.0001 |
| F-6.12.1-4 | 108 | 2 | 106 | 1.85 | 0.10 | 0.02-0.43 | 0.0003 |
| Control | 256 | 40 | 216 | 15.6 | 32.2 | 4.39-236 | <.0001 |

*F = Formula;
**Chi-Square, Pearson

The data indicated that feeding weaning infants with the products comprising N-acetylneuraminic acid and N-acetylglucosamine or N-acetylneuraminic acid and methionine significantly reduced the diarrhea of weaning infants. Thus the products comprising N-acetylneuraminic acid and N-acetylglucosamine or N-acetylneuraminic acid and methionine can be used for the prevention of diarrhea of weaning infants.

From about week three of weaning, some piglets showed the symptoms of difficult breath (asthma) called respiratory syndrome probably caused by respiratory infection. 9.72% of the piglets of the control group had the respiratory syndrome or asthma. 4.60% and 1.85% of the piglets of the two test groups showed the similar symptoms (Table 13). 6.02% of the piglets of the control group died from the respiratory syndrome or asthma; less than 1% of the piglets of the two test groups died from the similar symptoms (Table 14).

TABLE 12

The sick rates of weaning piglets with respiratory syndrome

| Group | N= | Sick | No sick | Rate(%) | OR (risk) | 0.95 CI | P** |
|---|---|---|---|---|---|---|---|
| *F-6.12.1-3 | 174 | 8 | 166 | 4.60 | 0.45 | 0.19-1.04 | 0.08 |
| F-6.12.1-4 | 106 | 2 | 104 | 1.89 | 0.18 | 0.04-0.78 | 0.01 |
| Control | 216 | 21 | 195 | 9.72 | 2.23 | 0.96-5.18 | 0.08 |

*F = Formula;
**Fisher Exact Probability Test (two-tailed)

TABLE 13

The death rates of weaning piglets with respiratory syndrome

| Group | N= | Death | No death | Rate (%) | OR (risk) | 0.95 CI | P** |
|---|---|---|---|---|---|---|---|
| *F-6.12.1-3 | 174 | 1 | 173 | 0.06 | 0.09 | 0.01-0.08 | 0.004 |
| F-6.12.1-4 | 106 | 1 | 105 | 0.94 | 0.15 | 0.02-1.15 | 0.04 |
| Control | 216 | 13 | 203 | 6.02 | 11.1 | 1.43-85.6 | 0.004 |

*F = Formula;
**Fisher Exact Probability Test (two-tailed)

The data indicated that feeding weaning piglets with the feeds with the products comprising N-acetylneuraminic acid and N-acetylglucosamine or N-acetylneuraminic acid and methionine significantly reduced the frequencies of sick and death of weaning infants suffer from respiratory syndrome or asthma. Thus the products comprising N-acetylneuraminic acid and N-acetylglucosamine or N-acetylneuraminic acid can be used for the prevention of respiratory syndrome or asthma and other diseases of weaning infants. The effective dosages of the formulas for the prevention of diarrhea, respiratory syndrome or asthma, and other diseases of weaning infants are from about 0.1 mg/kg to about 100 mg/kg of N-acetylneuraminic acid, N-acetyl glucosamine, or methionine. The amounts of ORS are from about 1 gram to about 5000 grams.

The other diseases of weaning infants include but not limited to respiratory infections, the respiratory syndrome, asthma, the infection of foot and mouth disease virus (FMDV), the infection of porcine circovirus (PCV) and other disorders of weaning infants 6.13 Prevention of Still Birth, Neonatal Death and Other Disorders of Pregnant and Feeding Sows 6.13.1. Formulations or Products Comprising N-acetylneuraminic Acid The major components of the formula mixture comprise N-acetylneuraminic acid and other optional components including oral rehydration salt (ORS) as described above in the example 1 if necessary. Examples of the formula or product comprising:

6.13.1-1 A powder mixture of N-acetylneuraminic acid:

A. 0.5-20 grams of N-acetylneuraminic acid;

B. 50-500 grams of ORS mixture.

6.13.2. Methods of Making

For manufacturing products of a dietary or nutritional supplement, a food or a feed or a food or feed additive, or a therapeutic product containing N-acetyl-neuraminic acid alone, adding suitable amounts of N-acetylneuraminic acid to the product and optional components including the ORS mixture, or other necessary materials known in the art, to form a tablet, a capsule, a pill, a powder mixture, a granule, an elixir, a tincture, a solution, a suspension, a syrup or a emulsion, a nasal drop or spray, an injectable, an infusion, or a form conjugated to a nano-particle, or other using forms well known to those of ordinary skill in the relevant arts.

Wherein in a product of a dietary or nutritional supplement, a food or a feed or a medicated food additive or medicated feed additive, or a therapeutic, the amounts or concentrations of N-acetylneuraminic acid are from about 0.1 mg/ml to about 900 mg/ml or 0.01 mg/g to about 900 mg/g, the amount of the ORS mixture are about 1.0-580 grams in a pack of powder mixture of about 500-600 grams.

6.13.2. Methods of Using

The formula-6.13.1-1 comprising N-acetylneuraminic acid, formula-6.12.1-3 comprising N-acetylneuraminic acid and N-acetyl glucosamine and the formula-6.12.1-4 comprising N-acetylneuraminic acid and methionine as mentioned above were tested with pregnant and feeding sows for the prevention of abortion, dystocia, still birth, neonatal death, mastitis and other diseases of sows.

Making Feed with Formulas a. Feed used: Premix lactation feed or sow feed without antibiotics (made in Belgium and Switzerland).b. Formula-6.13.1-1: mixing 4 grams of N-acetylneuraminic acid, and 250 grams of rehydration salt (vehicle) to form a powder mixture (about 254 g/pack).c. Feed with formulas: adding one pack (~254-258 g) of the powder mixture of formula-6.13.1-1 into 500 kg of the premix lactation feed or sow feed, and mix thoroughly. The final concentration of the formula in the lactation feed is about 8 mg/kg of each of N-acetylneuraminic acid (formula-6.13.1-1).

b. Control feed: adding one pack of ORS (~250 g) into 500 kg of the premix lactation feed or sow feed, and mix thoroughly. This feed without any formulas was used as control.

Method of Using

Prevention of Still birth, Neonatal Death and Other Disorders of Pregnant and Feeding Sows Pregnant sows: at 2-4 weeks before due date.

Test group: 29 of pregnant sows, fed with lactation feed or sow feed with formula-6.13.1-1 as mentioned above.

Control group: 29 of pregnant sows, fed with lactation feed or sow feed with ORS alone as mentioned above.

a. The lactation feeds were given between 1-3 weeks before delivery date.

b. The total feeding days with the lactation feeds or sow feeds were 5-10 days.

The Observed Results

7/29 of the pregnant sows of the control group had either abortion, dystocia, infections, or sudden death without clear causes; and only 2/29 of the pregnant sows of the test group with the feed of formula-6.13.1-1 had either abortion, or infection (Table 14). Three sows of the control group died from dystocia, infection, and sudden death, while none of the sows of the test group died. In addition, two sows of the control group had mastitis, and none of the sows of the test group had mastitis.

TABLE 14

The frequencies of pregnant sows with abortion, dystocia, infections and other disorders

| Group | Sow, N= | Abortion | Dystocia | Infection | Other* | Total | Rate(%) | OR (risk) | 0.95 CI | P** |
|---|---|---|---|---|---|---|---|---|---|---|
| F-6.13.1-1 | 29 | 1 | 0 | 1 | 0 | 2 | 6.45 | 0.29 | 0.29-1.49 | 0.16 |
| Control | 29 | 2 | 1 | 3 | 1 | 7 | 19.4 | 3.50 | 0.67-18.7 | 0.16 |

*Death without clear cause; F = Formula;

**Fisher Exact Probability Test (two-tailed)

32/216 (14.8%) of the newborns of the control group sows were died at delivery (still birth), and 6/215 (2.79%) of the test group sows were died at delivery. 11/216 (5.09%) of the newborns of the control group sows were died within two weeks after birth (neonatal death); and 5/215 (2.33%) of the newborns of the test group sows were died. The total deaths of still birth and neonatal death of the control group sows was 16.6% and the total deaths of still birth and neonatal death of the test group sows was 4,87% (Table 15).

TABLE 15

The frequencies of pregnant sows with still birth and neonatal death

| Group | Sow/piglet, N= | Still birth | Neo*death | Total | Rate(%) | OR (risk) | 0.95 CI | P** |
|---|---|---|---|---|---|---|---|---|
| F-6.13.1-1 | 29/215 | 6 | 5 | 11 | 4.87 | 0.26 | 0.13-0.51 | <.0001 |
| Control | 29/216 | 32 | 11 | 43 | 16.6 | 3.89 | 1.95-7.75 | <.0001 |

*Neo = Neonatal; F = Formula;

**Fisher Exact Probability Test (two-tailed).

In another two tests, similar results were observed with sows fed with feeds with either formula-6.12.1-3 or formula-6.12.1-4.

The data indicated that feeding pregnant sows with the feeds with either formul-6.13.1-1, or formul-6.12.1-3, or formula-6.12.1-4 significantly reduced the deaths due to still birth and neonatal death. Thus the products comprising N-acetylneuraminic acid alone, or products comprising N-acetylneuraminic acid and N-acetylglucosamine or methionine can be used for the prevention of still birth and neonatal death of pregnant females.

In addition, feeding pregnant females with the feeds with either formul-6.13.1-1, or formul-6.12.1-3, or formula-6.12.1-4 also reduced abortion, dystocia, mastitis, infections and other diseases of pregnant and feeding females.

The effective dosages of the products for the prevention of abortion, dystocia, still birth, neonatal death, infections, mastitis, and other diseases of pregnant and feeding females are from about 0.1 mg/kg to about 100 mg/kg of N-acetylneuraminic acid, N-acetylglucosamine, or methionine. The amounts of ORS are from about 1 gram to about 5000 grams. The other diseases of pregnant and feeding females include but not limited to respiratory infections, the respiratory syndrome, asthma, the infection of foot and mouth disease virus (FMDV), the infection of porcine circovirus (PCV), sudden death without clear causes, various infections and other disorders.

Prevention of Diarrhea of Newborn Piglets by Feeding Pregnant and Feeding Sows

Pregnant sows: at 1-10 days before delivery.

Test group-1: 30 of pregnant sows, fed with lactation feed with formula-6.13.1-1 as mentioned above.
Test group-2: 30 of pregnant sows, fed with lactation feed with formula-6.12.1-3 as mentioned above.
Test group-3: 50 of pregnant sows, fed with lactation feed with formula-6.12.1-4 as mentioned above.
Control group: 100 of pregnant sows, fed with lactation feed with ORS alone as mentioned above.
  c. The lactation or sow feeds were given between 1-10 days before delivery date.
  d. The total feeding days with the lactation feeds were 5-10 days.

The Observed Results

During a outbreak of diarrhea, over 90% of newborn piglets died from serious diarrhea within 5 days after birth. To reduce the death of the newborn piglets, the pregnant sows were treated either with the feed with formula-6.12.1-3, -6.12.1-4, or -6.13.1-1, or with feed mixed with the solutions of formula-2.2, or -6.12.1-2. Although the treatment of pregnant sows did not completely prevented the diarrhea of their newborns (Table 16) the deaths of newborn piglets were significantly reduced (Table 17).

TABLE 16

The diarrhea rates of nerborn piglets delivered to treated pregnant sows

| Group | N= | Diarrhea | No Diarrhea | Rate (%) | OR (risk) | 0.95 CI | P* |
|---|---|---|---|---|---|---|---|
| F-6.13.1-1 | 325 | 261 | 64 | 80.3 | 0.08 | 0.04-0.16 | <.0001 |
| F-6.12.1-3 | 331 | 249 | 82 | 75.2 | 0.06 | 0.03-0.12 | <.0001 |
| F-6.12.1-4 | 329 | 240 | 89 | 72.9 | 0.06 | 0.03-0.11 | <.0001 |
| Control | 549 | 538 | 11 | 97.8 | 11.9 | 6.22-23.1 | <.0001 |

F = Formula;
*Chi-Square, Pearson.

TABLE 17

The death rates of nerborn piglets delivered to treated pregnant sows

| Group | N= | Death | No Death | Rate (%) | OR (risk) | 0.95 CI | P* |
|---|---|---|---|---|---|---|---|
| F-6.13.1-1 | 325 | 99 | 226 | 30.5 | 0.07 | 0.05-0.10 | <.0001 |
| F-6.12.1-3 | 331 | 93 | 238 | 28.1 | 0.06 | 0.04-0.08 | <.0001 |
| F-6.12.1-4 | 329 | 87 | 242 | 26.4 | 0.06 | 0.04-0.08 | <.0001 |
| Control | 549 | 476 | 73 | 86.7 | 14.9 | 10.6-20.9 | <.0001 |

F = Formula;
*Chi-Square, Pearson.

The data indicated that treating pregnant females with the products comprising N-acetylneuraminic acid alone, or products comprising N-acetylneuraminic acid and N-acetylglucosamine or methionine significantly reduced the deaths of their newborn piglets due to serious diarrhea. Thus the products can be used on pregnant females for the prevention of the deaths of their newborn death due to serious diarrhea. The effective dosages of the products given to pregnant females for the prevention of newborn death due to serious diarrhea are from about 0.1 mg/kg to about 100 mg/kg of N-acetylneuraminic acid, N-acetylglucosamine, or methionine. The amounts of ORS are from about 1 gram to about 5000 grams.

The other diseases of females include but not limited to respiratory infections, the respiratory syndrome, asthma, the infection of foot and mouth disease virus (FMDV), the infection of porcine circovirus (PCV), sudden death without clear causes, various infections and other disorders.

Additional Definitions

As used herein, the term "treating" or "treatment" refers to clinical intervention (such as, e.g., administration of an immunoglobulin product, serum, or plasma, as described herein) designed to alter the natural course of the individual or cell being treated during the course of clinical pathology of a viral infection. Desirable effects of treatment include decreasing the rate of disease progression or mortality, ameliorating or palliating the disease state, and remission or improved prognosis. In some embodiments, the treatment improves symptoms of viral infection (e.g., an influenza viral infection), reduces frequency or severity of the disease caused by the viral infection (e.g., influenza), and/or improves patient-reported symptoms (e.g., such as symptoms of influenza, including, but not limited to, e.g., fever, chills, cough, sore throat, body aches, and fatigue). A response is achieved when the patient experiences partial or total alleviation, or reduction of signs or symptoms of illness, and, in some embodiments, includes survival. A subject is successfully "treated," for example, if one or more symptoms associated with a viral infection (such as influenza) are mitigated or eliminated.

As used herein, the term "preventing" or "prevention" includes providing prophylaxis with respect to occurrence or recurrence of viral infection (such as influenza) in an individual. An individual may be predisposed to or susceptible to viral infection (such as infection by an influenza virus), but has not yet been infected with the virus.

As used herein, an individual "at risk" of viral infection (such as influenza infection) denotes that an individual is likely to be exposed to a viral pathogen or has one or more risk factors of having severe reactions to viral pathogen if infected.

An "effective amount" refers to at least an amount of immunoglobulin product, serum or plasma, as described herein, that is effective, at dosages and for periods of time necessary, to achieve the desired or indicated effect, including a therapeutic or prophylactic result. An effective amount can be provided in one or more administrations.

As used herein, the term "patient" or "individual" refers to a mammal, including, but not limited to, a human or non-human mammal, such as a bovine, equine, porcine, canine, ovine, or feline. In some embodiments, the patient or individual is a human. In some embodiments, the patient is not in need of a blood transfusion due to, e.g., an injury or bleeding clotting disorder such as, but not limited to, e.g., hemophilia, von Willebrand disease, and leukemia.

As used herein, the patient in the present invention comprises human or non-human mammal of males and females, newborns, 1-12 months old infants, 1-18 years old, adults, pregnant and feeding females, and pregnant or feeding females with their fetus or sucking babies at risk of suffering or developing the diseases and conditions caused by harmful antibodies.

Additional Embodiments

1. A product for treating and preventing infectious or inflammatory diseases wherein the product is in a composition comprising N-acetylneuraminic acid or N-acetylneuraminic acid and at least one of:
   a. An analog of N-acetylneuraminic acid
   b. A methionine
   c. Another saccharide
   d. A therapeutic
   wherein the product is one of a nutritional supplement, a food, a feed, a medicated food additive, a medicated feed additive, a therapeutic product, a rehydration salt, or a rehydration solution.
   wherein the infectious and inflammatory diseases are caused by viral or bacterial infections, gastroenteritis, nutritional problems or food intolerances, inflammation or allergy, gastrointestinal and respiratory diseases or conditions, cancers and autoimmune diseases.
2. The product of embodiment 1, wherein the product is in a form of tablets, capsules, pills, powders, granules, elixirs, tinctures, solutions, suspensions, syrups and emulsions, nasal drops or sprays, an injectable, an infusion, or a form conjugated to a nano-particle.
3. The product of embodiment 1, wherein the analog of N-acetylneuraminic acid is N-acetylneuraminic acid methyl ester; the another saccharide comprises 2-Keto-3-deoxynononic acid, N-Acetylglucosamin, N-Acetylgalactosamine, N-Acetylmannosamine, N-Glycolylneur-aminic acid, fructose, glucose, mannose, fucose, xylose, galactose, lactose; the therapeutics comprise antibiotics and interferon.
4. The product of embodiment 3, wherein the antibiotic is Tamiflu, Enrofloxacin, Timicosin, Cephradine, or Tulathromycin.
5. The product of embodiments 1 or 3 or 4, wherein the product is in a composition comprising about 0.1 mg/ml to about 20 mg/ml or about 0.1 mg/g to about 20 mg/g of the N-acetylneuraminic acid, or the analog of N-acetylneuraminic acid, or the methionine, or the another saccharide, or the antibiotic wherein the amount of the antibiotic is reduced to about 10% to 75% of the amount of the antibiotic being used alone.
6. The product of embodiments 1 or 3, wherein the product is in a composition comprising N-acetylneuraminic acid and N-acetylglucosamine at a concentration between about 0.1 mg/ml to about 20 mg/ml or about 0.1 mg/g to about 20 mg/g of the N-acetylneuraminic acid and about 0.1 mg/ml to about 20 mg/ml or about 0.1 mg/g to about 20 mg/g of the N-acetylglucosamine; wherein the product is a nutritional supplement, a food, a feed, a medicated food additive, a medicated feed additive, a therapeutic product, a rehydration salt, or a rehydration solution.
7. The product of embodiments 1 or 3 or 4, wherein the product is in a composition comprising N-acetylneuraminic acid and an antibiotic at a concentration between about 0.1 mg/ml to about 20 mg/ml or about 0.1 mg/g to about 20 mg/g of the N-acetylneuraminic acid and reduced amount of the antibiotic; wherein the amount of the antibiotic is reduced to about 10% to 75% of the amount of the antibiotic being used alone; wherein the product is a nutritional supplement, a food, a feed, a medicated food additive, a medicated feed additive, a therapeutic product, a rehydration salt, or a rehydration solution.
8. A method of making a product of embodiments 1-7 by adding N-acetylneuraminic acid to a composition wherein the concentration of the N-acetylneuraminic acid in the composition is between about 0.1 mg/ml to about 20 mg/ml or about 0.1 mg/g to 20 mg/g; or adding N-acetylneuraminic acid and at least another component to a composition, wherein the another component comprises at least one of:
   i. Another saccharide, wherein the concentration of the saccharide in the product is between about 0.1 mg/ml to about 20 mg/ml or between about 0.1 mg/g to about 20 mg/g.
   ii. A therapeutic or an antibiotic, wherein the amount of the antibiotic is about 10% to 75% of the amount of the antibiotic being made alone.
   wherein the product is a nutritional supplement, or a food, or a feed, or a medicated food additive, or a medicated feed additive, or a therapeutic product, or a rehydration salt or a rehydration solution.
9. The method of embodiment 8, wherein the another saccharide is 2-Keto-3-deoxynononic acid, N-Acetylglucosamin, N-Acetylgalactosamine, N-Acetylmannosamine, N-Glycolylneur-aminic acid, fructose, glucose, mannose, fucose, xylose, galactose, or lactose, the therapeutic is antibiotic or interferon, the antibiotic is Tamiflu, Enrofloxacin, Timicosin, Cephradine, or Tulathromycin.
10. A method for treating or preventing an infectious disease or inflammatory disease or infection-relating diseases or conditions, comprising administering an effective amount of at least one of the product of claim 1-6 to a patient who has been diagnosed with an infectious disease or an inflammatory diseases or an infection-relating diseases or conditions, or who is at risk for an infectious or inflammatory disease, or an infection-relating diseases or conditions.
   wherein the infection-relating disease or condition is occurred during or after an infection or a vaccination.
11. The method of embodiment 10, wherein the infectious disease is caused by a viral or bacterial infection; the inflammatory diseases is caused by gastroenteritis, nutritional problems or food intolerances, inflammation or allergy, gastrointestinal and respiratory diseases or conditions, cancers and autoimmune diseases.
12. The method of embodiment 10-11, wherein the infectious disease is a viral infection; the infection-relating disease or condition is a gastrointestinal or respiratory disorder, abortion, dystocia, still birth, neonatal death and sudden death of pregnant females caused by an infection. wherein the inflammatory disease is rhinitis, sinusitis, arthritis, essential tremor and Parkinson's disease, pollen allergy, or mastitis of feeding females.
13. The method of embodiment 11-12, wherein the viral infection is caused by an influenza virus, a Newcastle disease virus, a rotavirus, a foot and mouth disease virus (FMDV), a porcine circovirus (PCV) and HCV; the gastrointestinal disorders are diarrhea, dehydration due to diarrhea or fever; gastrointestinal inflammation, the respiratory disorders are respiratory inflammation, chronic reparatory syndrome, and asthma.

14. The method of embodiment 10, wherein the effective amount of the at least one of the products of claim 1-7 is between about 0.1 mg/kg to about 20 mg/kg of the N-acetylneuraminic acid, or about 0.1 mg/kg to about 20 mg/kg of the N-acetylneuraminic acid and at least one of about 0.1 mg/kg to about 20 mg/kg of the analog of N-acetylneuraminic acid, or the methionine, or the another saccharide, or the antibiotic wherein the amount of the antibiotic is reduced to about 10% to 75% of the amount of the antibiotic being used alone.

15. The method of embodiment 10, wherein the at least one of the products of claims 1-6 is administered subcutaneously, topically, orally, intramuscularly, intravenously, intraperitoneally, intracavitally, or transdermally, or via inhalation.

16. The method of embodiment 10, wherein the patient is an animal; wherein the animals are livestocks comprising cows, pigs, horses, sheep or goats, llamas, cattle, donkeys; poultry comprising chickens, ducks, gooses, turkeys and pigeons; companion animals comprising dogs, cats, rodent pets and avian pets, aquatic animals comprising fish, shrimp, oyster, crustaceans, and molluscs.

17. The method of embodiment 16, wherein the animals comprise males and females, adult, newborns, sucking infants, weaning infants, and other young age animals, pregnant and feeding females.

18. The method of embodiment 10, wherein the patient is a human; wherein the humans comprising males and females, newborns, 1-12 months old infants, 1-18 years old children, adults, old people, pregnant and feeding females.

The invention claimed is:

1. A method for treating an infectious disease, inflammatory disease or infection-relating disease or condition, the method comprising administering an effective amount of a composition to a patient diagnosed with an infectious disease, inflammatory disease or an infection-relating disease or condition, wherein the composition comprises:
    (a) about 0.01 mg/mL to about 20 mg/mL of N-acetylneuraminic acid;
    (b) about 0.01 mg/mL to about 20 mg/mL of N-acetylneuraminic acid methyl ester; and
    (c) about ¼ to about ¾ of the manufacturer's recommended dose of Tamiflu for the treatment of influenza; or
    (d) about ¼ to about ¾ of the manufacturer's recommended dose of Enrofloxacin for the treatment of rotavirus infection or diarrhea; or
    (e) about ¼ to about ¾ of the manufacturer's recommended dose of Cephradine for the treatment of diarrhea gastroenteritis; and
    wherein the infectious disease, inflammatory disease or an infection-relating disease or condition is gastroenteritis, diarrhea, or viral infection caused by influenza or rotavirus.

2. The method of claim 1, wherein the administration is subcutaneous, topical, oral, intramuscular, intravenous, intraperitoneal, intracavital, or transdermal, or via inhalation.

3. The method of claim 1, wherein the patient is an animal, wherein the animal is a cow, pig, horse, sheep, goat, llama, cattle, donkey, chicken, duck, goose, turkey, pigeon, a dog, a cat, a rodent, bird, a fish, a shrimp, an oyster, a crustacean, or a mollusk.

4. The method of claim 1, wherein the patient is a human.

5. A method for treating an infectious disease, inflammatory disease or infection-relating disease or condition with a reduced amount of antibiotic, the method comprising:
    administering to a patient diagnosed with an infectious disease, inflammatory disease or an infection-relating disease or condition an effective amount of a composition comprising N-acetylneuraminic acid or N-acetylneuraminic acid and an antibiotic,
    wherein the composition comprises an amount of the antibiotic is about 10% to about 75% less than the amount of the antibiotic if the antibiotic had been used alone, and
    wherein the infectious disease, inflammatory disease or an infection-relating disease or condition is gastroenteritis, diarrhea, or viral infection caused by influenza or rotavirus.

6. The method of claim 5, wherein the composition further comprises at least one of:
    N-acetylneuraminic acid methyl ester; or
    a methionine.

* * * * *